(12) United States Patent
Ubelhor et al.

(10) Patent No.: US 10,288,497 B2
(45) Date of Patent: May 14, 2019

(54) APPARATUS FOR DESTRUCTIVE EVENT TESTING OF CHEMICAL ENERGY SYSTEMS USING ADAPTIVE HEAT FLOW TESTING SYSTEMS AND RELATED METHODS

(71) Applicant: The United States of America as represented by the Secretary of the Navy, Washington, DC (US)

(72) Inventors: Ryan Ubelhor, Solsberry, IN (US); Daniel Ellison, Odon, IN (US); Cecilia Pierce, Bedford, IN (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 108 days.

(21) Appl. No.: 15/226,604

(22) Filed: Aug. 2, 2016

(65) Prior Publication Data

US 2016/0341609 A1     Nov. 24, 2016

Related U.S. Application Data

(63) Continuation-in-part of application No. 14/539,241, filed on Nov. 12, 2014, now Pat. No. 9,739,670.
(Continued)

(51) Int. Cl.
*G01K 19/00* (2006.01)
*G01N 25/32* (2006.01)
(Continued)

(52) U.S. Cl.
CPC ............ *G01K 19/00* (2013.01); *G01K 17/00* (2013.01); *G01N 25/20* (2013.01); *G01N 25/32* (2013.01)

(58) Field of Classification Search
CPC ......... G01K 19/00; G01K 17/00; G01N 25/20
(Continued)

(56) References Cited

U.S. PATENT DOCUMENTS 4,859,077 A * 8/1989 Ito ..................... G01N 25/4846
374/31
4,892,707 A * 1/1990 Stockton ............ G01N 25/4846
374/31

(Continued)

OTHER PUBLICATIONS

"A Unique Calorimeter-Cycler for Evaluating High-Power Battery Modules", by Ahmad A. Pesaran, Donald J. Russell, John W. Crawford, Robert Rehn, and Edwin A. Lewis; 5 pages.

*Primary Examiner* — Nathaniel T Woodward
(74) *Attorney, Agent, or Firm* — Christopher A. Monsey

(57) ABSTRACT

Apparatus and methods are provided for providing flexible and repairable testing capabilities, including destructive testing, for systems that generate or absorb heat such as energy storage systems. One embodiment can include a temperature bath structure adapted to contain and maintain a fluid bath at a predetermined temperature, an outer containment structure adapted to insert into the temperature bath structure, heat sinks, thermal sensor assemblies, and an internal containment structure where the thermal sensor assemblies, heat sinks removeably attach to different sections of the inner containment structure so as to measure heat flow into or out of the inner containment structure's different sections, and a test cell enclosure which is adapted to contain forces and output from destructive testing of samples. Embodiments of the invention enable rapid insertion/removal of samples as well as replacement of sections of the system including thermal sensor assemblies as well as enabling separate thermal measurements associated with different sections of a sample under test.

17 Claims, 22 Drawing Sheets

Related U.S. Application Data

(60) Provisional application No. 62/200,535, filed on Aug. 3, 2015, provisional application No. 62/035,738, filed on Aug. 11, 2014.

(51) Int. Cl.
*G01N 25/20* (2006.01)
*G01K 17/00* (2006.01)

(58) Field of Classification Search
USPC ............... 374/1, 2, 3, 4, 5, 31, 33, 34, 208; 702/127, 130, 136
See application file for complete search history.

(56) References Cited

U.S. PATENT DOCUMENTS

| | | | | |
|---|---|---|---|---|
| 4,923,306 A | * | 5/1990 | Fauske | G01K 17/00 165/11.1 |
| 6,824,306 B1 | * | 11/2004 | Fesmire | G01N 25/18 374/34 |
| 2014/0003460 A1 | * | 1/2014 | Keyser | G01K 17/00 374/31 |
| 2016/0025661 A1 | * | 1/2016 | Jossens | G21C 19/40 374/10 |

* cited by examiner

APPARATUS FOR DESTRUCTIVE EVENT TESTING OF CHEMICAL ENERGY SYSTEMS USING ADAPTIVE HEAT FLOW TESTING SYSTEMS AND RELATED METHODS

CROSS-REFERENCE TO RELATED APPLICATIONS

The present application claims priority to U.S. Provisional Patent Application Ser. No. 62/200,535, filed on Aug. 3, 2015, entitled "APPARATUS FOR DESTRUCTIVE EVENT TESTING OF CHEMICAL ENERGY SYSTEMS USING ADAPTIVE HEAT FLOW TESTING SYSTEMS AND RELATED METHODS," and is related to U.S. patent application Ser. No. 14/539,241, filed Nov. 12, 2014, entitled "ADAPTIVE HEAT FLOW CALORIMETER," which claims priority to U.S. Provisional Patent Application Ser. No. 62/035,738, filed Aug. 11, 2014, entitled "ADAPTIVE HEAT FLOW CALORIMETER," the disclosures of which are expressly incorporated by reference herein.

STATEMENT REGARDING FEDERALLY SPONSORED RESEARCH OR DEVELOPMENT

The invention described herein was made in the performance of official duties by employees of the Department of the Navy and may be manufactured, used and licensed by or for the United States Government for any governmental purpose without payment of any royalties thereon. This invention (Navy Case 200,266) is assigned to the United States Government and is available for licensing for commercial purposes. Licensing and technical inquiries may be directed to the Technology Transfer Office, Naval Surface Warfare Center Crane, email: Cran_CTO@navy.mil.

BACKGROUND AND SUMMARY OF THE INVENTION

Aspects of the present invention relates to performance and safety characterization or assessment systems and processes. In particular embodiments of the invention are directed to apparatus and methods for safety and performance characterization capable of operating before, during, and after a destructive event from a system or item under test.

Calorimetry can include processes of measuring an amount of heat released or absorbed during a chemical reaction. Calorimetry can be used in a wide range of material analysis across multiple industries. An Accelerating Rate calorimeter (ARC) method is one method used where a material sample is placed within an oven type enclosure. Temperature within the enclosure is elevated through multiple step increases with rest periods at each step. This increase continues until the sample reaches a thermal runaway condition where the heat release of the sample can be recorded.

For battery characterization the ARC methodology is questionable as the increasing heat may not be representative of real world conditions and may impact data collection. Lithium battery heat generation, as it approaches thermal runaway, is of interest as well as what occurs during the event.

A new approach can include use of isothermal calorimetry methodology where the cell's ambient temperature is controlled tightly during actual testing. This exemplary approach allows for an accurate evaluation of heat generated from chemical reactions or physical changes occurring within the cell. A goal can include use of various embodiments of the invention to evaluate isothermal calorimetry as a potential method for characterizing the potential energy release during a destructive event, the impact to surrounding environment, and risk mitigation development.

According to an illustrative embodiment of the present disclosure, embodiments of the invention include exemplary processes and associated equipment to adapt or construct a heat flow calorimeter to accept a sealed pressure vessel. In some embodiments, an apparatus is provided that combines a robust sample environment of a closed bomb (to enable overcharge, burn, detonation, etc of any sample in the closed bomb) with a highly sensitive detection capability including heat flow calorimetry. In particular, some embodiments have been constructed containing a pressure vessel in a sample chamber of the calorimeter for sample materials that would then be forced fully through decomposition. In some embodiments, an exemplary system included a pressure vessel and a capacity for deliberate overcharging of Lithium containing batteries in order to determine resulting pressure and heat energy released.

Also, efforts to obtain increased energy density of battery cells highlight a need for electrochemical techniques as well as additional characterization methods for these cells in order to meet user needs and safety requirements. In particular, a continuing need has called forth inventive efforts for developing novel calorimeters to satisfy various requirements for requiring activities including high energy density systems such as chemical energy storage systems, propellant, explosive, and pyrotechnic devices. To support optimization of electro chemical energy storage systems in particular it is necessary to understand their thermal characteristics at rest and under prescribed charge and discharge cycles. In one example, a need existed to develop a calorimeter system able to accommodate multiple battery cell configurations and provide empirical system data for use in modeling and simulation. Heat capacity, and thermal efficiency for each battery cell were determined, as well as the actual heat load from each surface of the cell. The heat flow from each of six surfaces of the cell and overall thermal efficiency were obtained with the cell at rest and under a variety of prescribed charge and discharge cycles representative of typical usage of these cells. Testing was completed isothermally at 25° C. to capture the requirements necessary to remove the entire generated thermal load from the battery cell. Moreover, these needs also included a requirement to create testing systems which are capable of larger testing capabilities that necessarily include a need to use larger systems, create more testing options with respect to samples under test, and create an ability to more cost effectively repair or replace costly components in such test systems which existing systems do not accommodate in a cost or time effective manner. As systems are scaled up in size, there is a higher level of failures in system components which require new designs to accommodate repairs or maintenance rather than throwing out large sub-assemblies. Also, there is a need to be able to swap out components for greater customized design or configurability of testing systems with respect to desired testing processes or data collection.

As an example of one embodiment, an improved measuring cell for a temperature bath was designed and constructed to measure the heat flow of larger cells (e.g., 18×8×16 cm). Heat flows from 0.01 to 7.00 Watts were measured with an average signal noise less than 1 mW. In one example, heat capacities of samples were also determined with experimental deviation of less than 2%.

Embodiments of the invention can include apparatus and methods for providing flexible and repairable testing capabilities for systems that generate or absorb heat such as energy storage systems. One embodiment can include a temperature bath structure adapted to contain and maintain a fluid bath at a predetermined temperature, an outer containment structure adapted to insert into the temperature bath structure, heat sinks, thermal sensor assemblies, an internal containment structure, and thermal barriers between different elements of the invention to isolate different sections from each other. An embodiment of the invention can include a system where the thermal sensor assemblies and heat sinks removeably attach to different sections of the inner containment structure so as to measure heat flow into or out of the inner containment structure's different sections without being altered by direct thermal contact with other inner containment sections. Embodiments of the invention permits rapid insertion/removal of samples as well as replacement of sections of an exemplary system including embodiments or parts of the thermal sensor assemblies as well as providing an ability to obtain separate thermal measurements associated with different sections of a sample under test within the inner containment structure. Other aspects of the invention include a capability to insert or substitute existing components such as containment structure elements, thermal sensors etc. with different sized elements or structures to accommodate different types of samples or differently sized samples under test. Embodiments can include electrical bus or wiring structures such as separate wiring sections and quick disconnects that also permit rapid repairs or alteration of configurations of various aspects of embodiments of the invention.

Existing systems do not provide a needed capability in a variety of areas including chemical battery testing. For example, existing systems might provide the closed bomb and low sensitivity or alternatively heat flow sensitivity but much stricter sample environment but not a combination thereof.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

Generally, one exemplary embodiment of an improved calorimeter test system has been designed to accept different sizes, e.g., two different sizes, of silver zinc based battery cells. The exemplary cells under test provided access to their normal electrical test system through a use of extended charging cables. Exemplary calorimeter test systems have been created to approximate operational conditions in which the test cell is operated isothermally at, e.g., 25° C. Maintaining an isothermal operating environment can be achieved through the use of a precision temperature bath. Exemplary test systems can be designed such that each of six surfaces of an exemplary test cell (cuboid sample) can be provided a thermal conduction pathway of least resistance that can be isolated from the other five surfaces and channeled through a plurality of thermopiles. In this example, exemplary thermopiles function according to the Seebeck effect and generate a voltage corresponding to a temperature difference on either side of the precision measurement device. A plurality of thermoelectric junctions in each thermopile amplifies this effect and thus lowers a minimum temperature difference required to generate a voltage to nearly isothermal values. In addition, embodiments have been created which provide an ability to create a reconfigurable test apparatus which permits different types of test cell enclosure (e.g., swapping one type of inner containment structure 15 with another type of test cell containment structure, e.g., see FIG. 22) to be used including a test cell containment structure that can be used with destructive testing that can generate, e.g., heat, bursting of a test article, or an explosion in a test article with an ability to obtain test results before, during, and after a destructive test event without causing damage to the overall testing apparatus.

Figure 1:
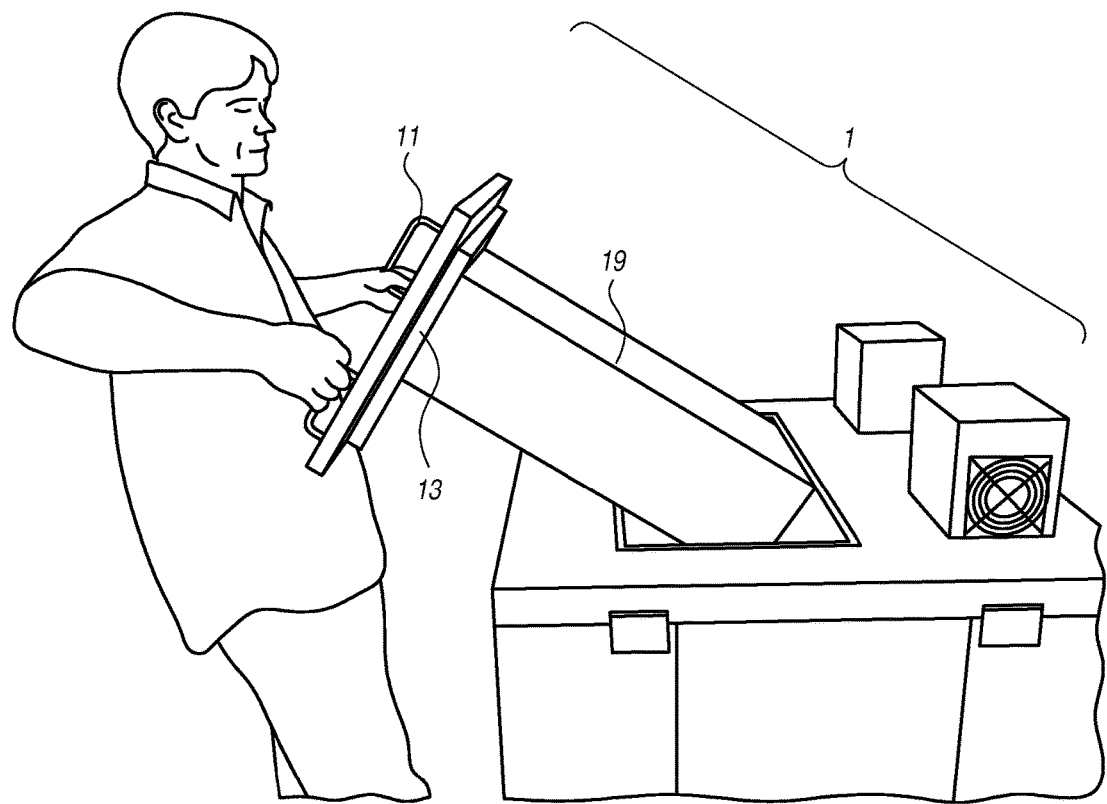
FIG. 1 shows an exemplary calorimetric system being removed from a precision temperature bath in accordance with one embodiment of the invention.

FIG. 1 shows maneuverability of an exemplary embodiment of a calorimetric measuring unit assembly 1. A user simply grasps handle 11 attached to a lid 13 in an outer containment structure 19 and pulls outwardly to extract outer containment structure 19 from fluid bath 9 (not shown in FIG. 1).

Figure 2:
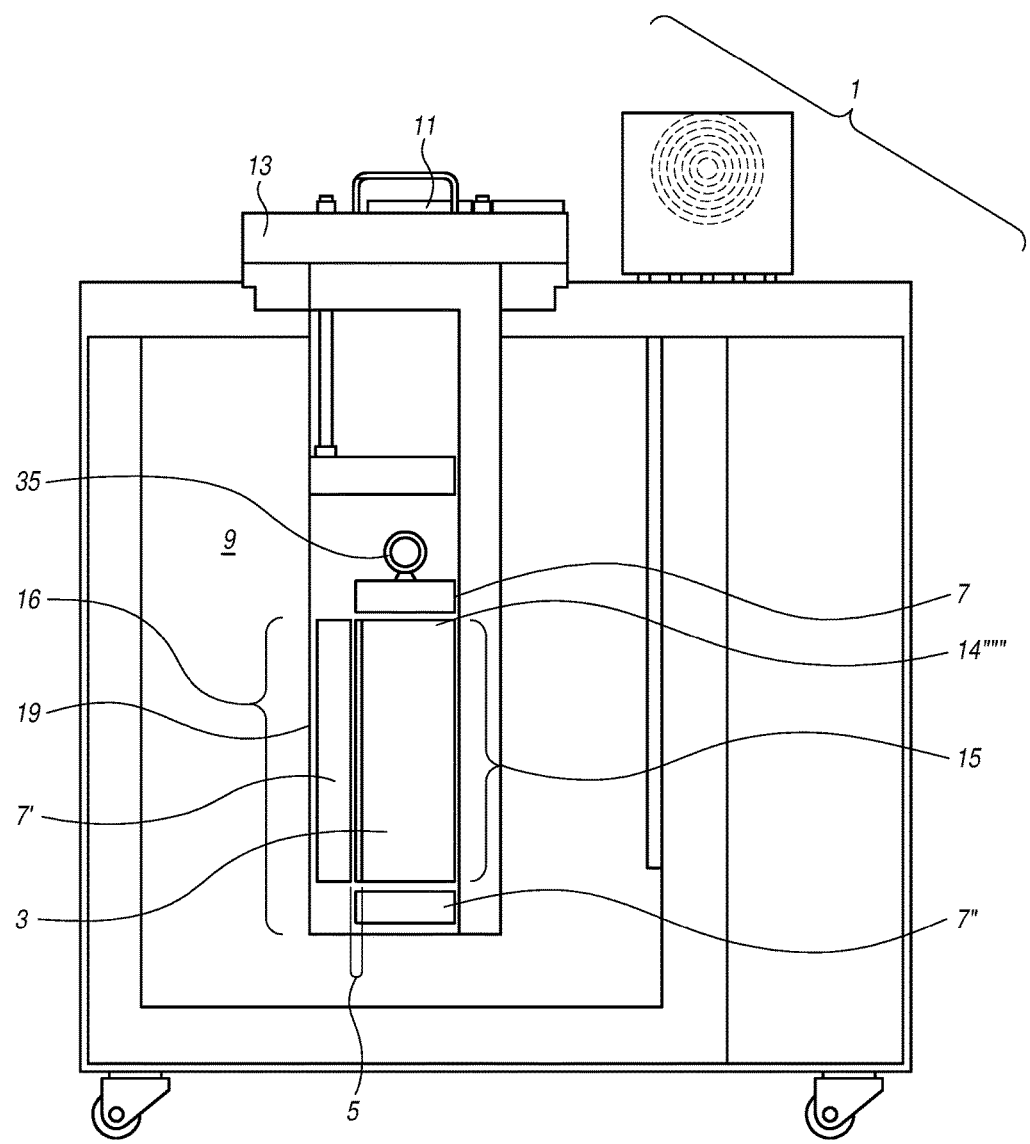
FIG. 2 shows a simplified perspective view of a battery cell under test inside an exemplary calorimetric measuring unit installed in a precision temperature bath in accordance with one embodiment of the invention.

FIG. 2 shows a simplified diagram of a tested sample 3 inside an exemplary calorimetric measuring unit 1 installed in an exemplary precision temperature measurement bath 9. In one embodiment, a sample 3 can be a battery. Exemplary sensor assembly 5 can be seen between an exemplary inner containment structure 15 which includes inner containment structure sections, e.g., section 14'''' (e.g. a top side)(see FIGS. 2 and 3 for more exemplary details), holding the sample 3 and heat sink 7'. In one embodiment a thermal isolation barrier 17 (shown in, e.g., FIGS. 5 and 6) can be located between edges of inner containment structure 15 and edges of each sensor assembly 5. Thermal isolation barriers 17 span a portion along edge sections of inner containment structure 15 and are provided to thermally isolate each wall of inner containment structure 15 from other adjacent walls to avoid unmeasured thermal contributions to each sensor assembly 5 thermally coupled to its respective wall of the inner containment structure 15 (e.g., thermal cross talk or undesired thermal energy migration between walls or segments associated with different thermocouples or thermopiles). Exemplary aspects of an embodiment of the invention as described herein allows for calorimetric measuring unit 1 to measure heat flow from each side of sample 3 independent of other sides.

In one embodiment, side, top, and bottom assemblies inside of outer containment structure 19 can include thermal isolation barriers sections 17, sensor assembly 5, and heat sink 7' where each applicable assembly is respectively coupled to each side, top, and bottom of the inner containment structure 15. Heat sinks 7, 7', etc. can be large enough with a high enough heat capacity such that thermal energy released through any sample's face is absorbed into heat sinks 7, 7', etc. However, thermal energy released from sample 3 and through elements of calorimetric measuring unit 16 is not enough to change the temperature of the heat sinks. Thermal energy absorbed by heat sinks 7, 7', etc. then dissipates through outer containment structure 19 and into a thermally stable fluid bath 9. Exemplary aspects of this invention as described herein also allows for calorimetric measuring unit 1 to have an increased capacity for samples that are larger and have higher heat load capacities. A high capacity heat sink 7 also helps to maintain an isothermal operating environment.

Figure 5:
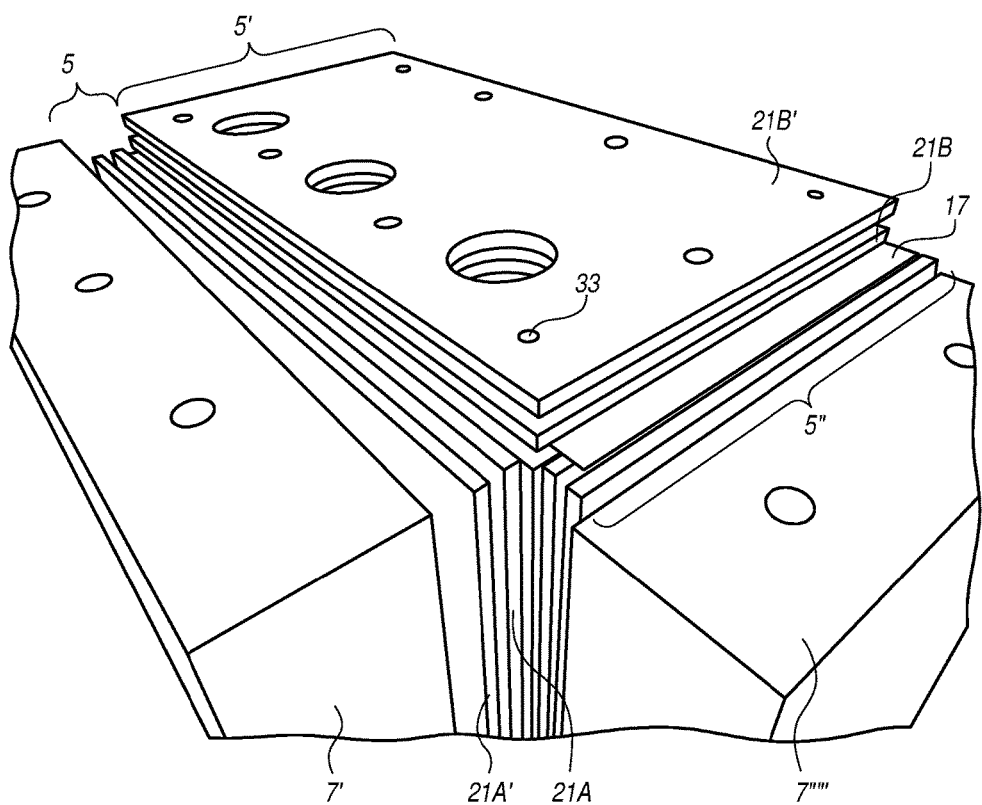
FIG. 5 shows an exemplary embodiment of an exemplary calorimetric measuring unit of an exemplary calorimetric measuring system with a top heat sink removed in accordance with one embodiment of the invention.

In one exemplary embodiment, each of heat sinks 7, 7', 7'', etc. are connected with respective surfaces of inner containment structure 15 with thermally non-conductive bolts (not shown) similar to the one 33 shown in FIG. 5 on the top heat sink. An embodiment can also include a lifting eye bolt 35 which aids in positioning the inner containment structure 15 inside the outer containment structure 19 for operation.

Referring back to FIG. 2, an embodiment can include cables (not shown) that connect to sample 3 which permit operation of a sample e.g., battery which permit calorimetric testing of a sample under operational test or use configurations. These cables can carry charge from a charging system (not shown) to sample 3 when testing and generating data for sample 3 in the calorimetric measuring unit 16. The exemplary calorimetric measuring unit 1 can also have a handle 11 for removal of outer containment structure 19, and lid 13 enclosing outer containment structure 19. The lid 13 can be removeably attached to the outer containment structure to permit the lid to be opened and closed after removal or insertion into the calorimetric measuring unit 1.

Figure 3:
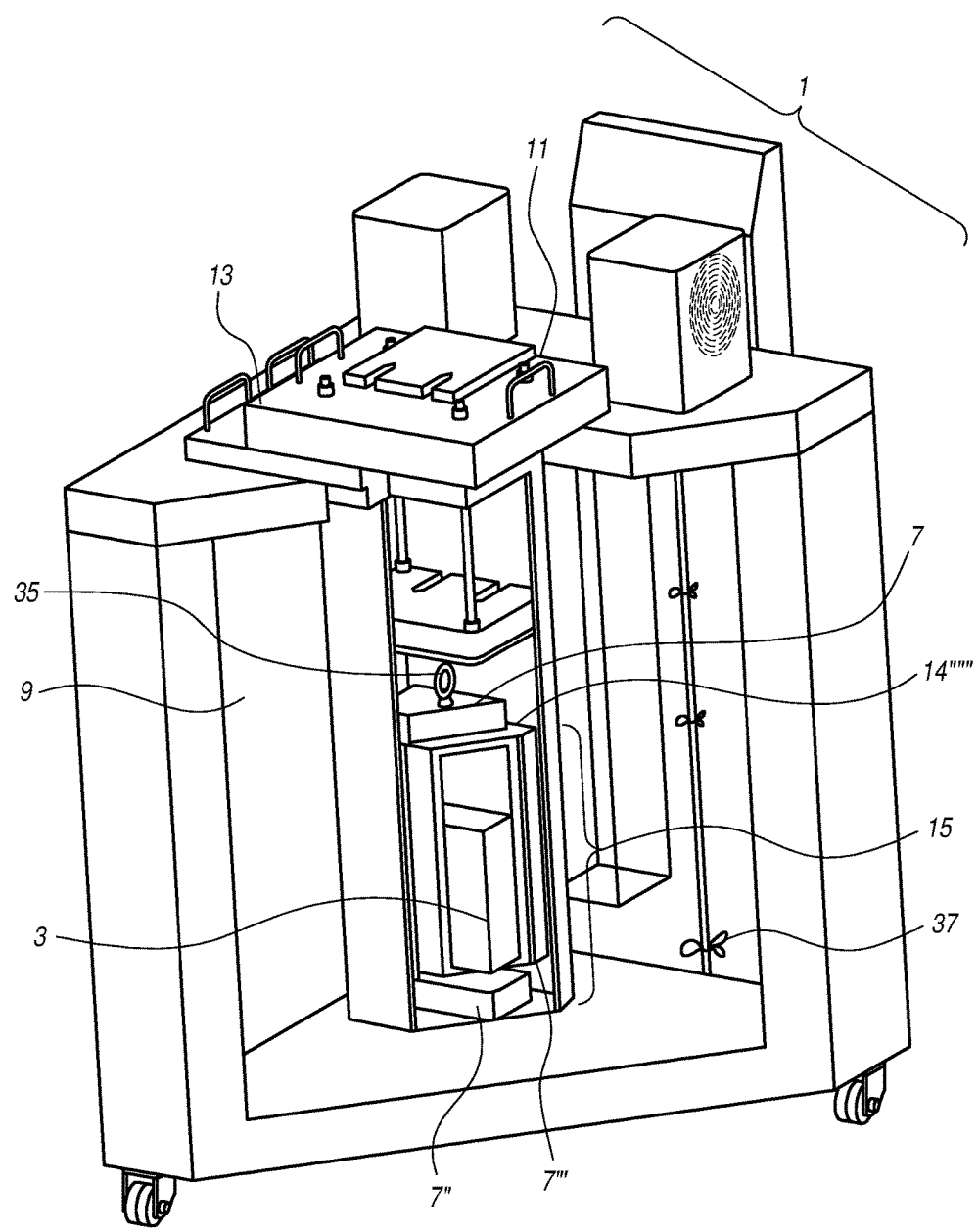
FIG. 3 shows positioning of an exemplary calorimetric measuring unit in an exemplary fluid bath in accordance with one embodiment of the invention.

An example of positioning of an exemplary calorimetric measuring cell in the fluid bath can be seen more clearly in FIG. 3. FIG. 3 shows a perspective cut-away view of the exemplary assembly shown in FIG. 2 but it also shows a stirrer 37 operable to mix the fluid bath in a predetermined manner to further control a temperature of fluid bath 9.

In one exemplary embodiment of calorimetric measuring system 1, a temperature control mechanism in fluid bath 9 can be provided. Exemplary temperature control mechanism can comprise an integrated heater (not shown) in a bottom plate of the fluid bath 9 and a cooling element (not shown) inserted into fluid bath 9 adapted to serve as an adjustable heat exchanger for fluid bath 9 located at a top portion of fluid bath 9. Heating or cooling elements can also be placed onto different locations of said fluid bath.

Figure 4:
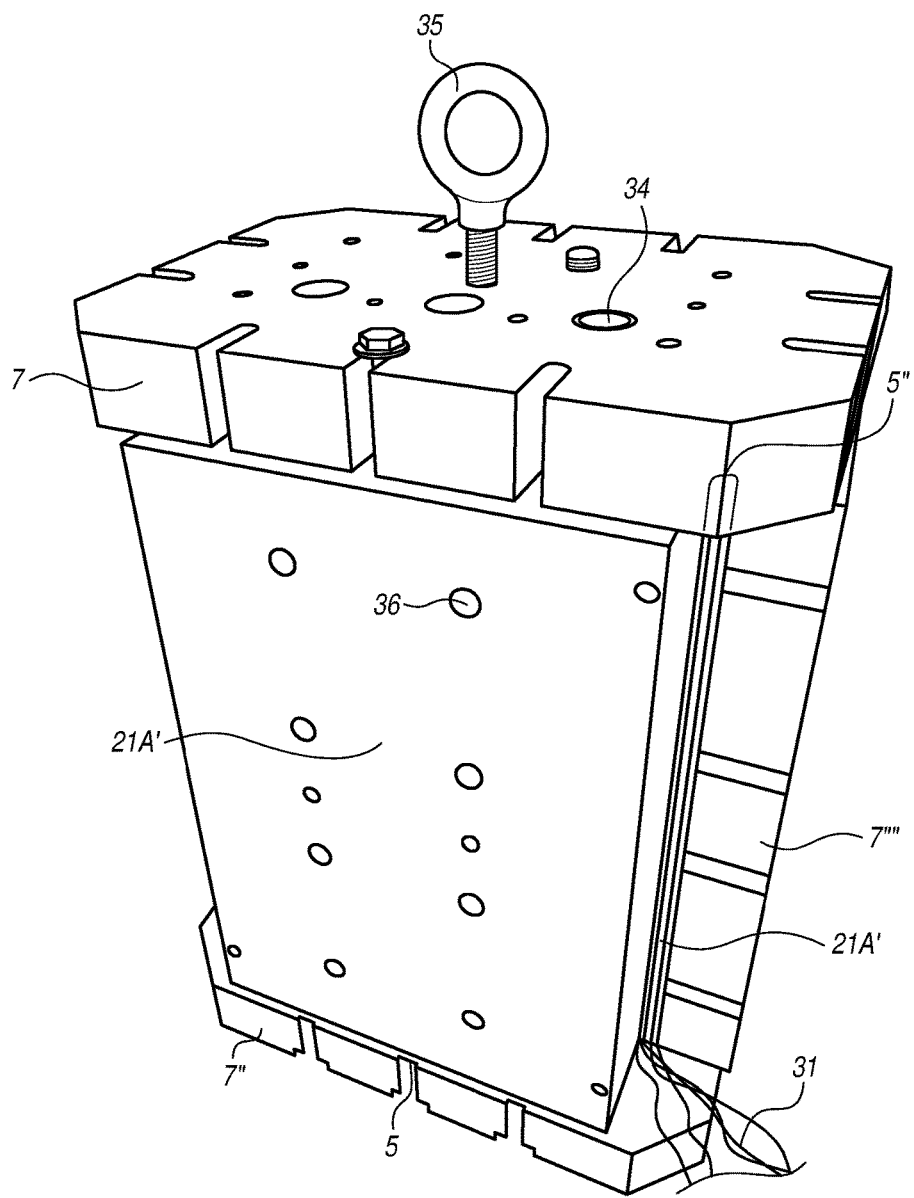
FIG. 4 shows a calorimetric measuring unit of an exemplary calorimetric measuring unit with a heat sink removed in relation to an exemplary embodiment of the invention.

Referring to FIG. 4, each exemplary heat sink 7, 7', etc., can be respectively thermally coupled to a different respective surface or section of inner containment structure 15 by non-heat conductive bolts (not shown) that insert into recessed areas 36 of the heat sinks in one embodiment. FIG.

4 also shows an outer thermally conductive surface 21A' of thermal sensor assembly 5 which is positioned to thermally couple with adjacent structures (e.g., inner containment structure 15 or heat sinks, e.g., 7), as well as wires 31 attached to thermal sensors in thermal sensor assembly 5. In this example, wires 31 carry electrical signals corresponding to measurement values from thermopiles for each side (23A, 23C, etc.) of the inner containment structure 15 to a data acquisition device 25 (not show in FIG. 4 but, e.g., shown in FIGS. 8 and 11).

Figure 6:
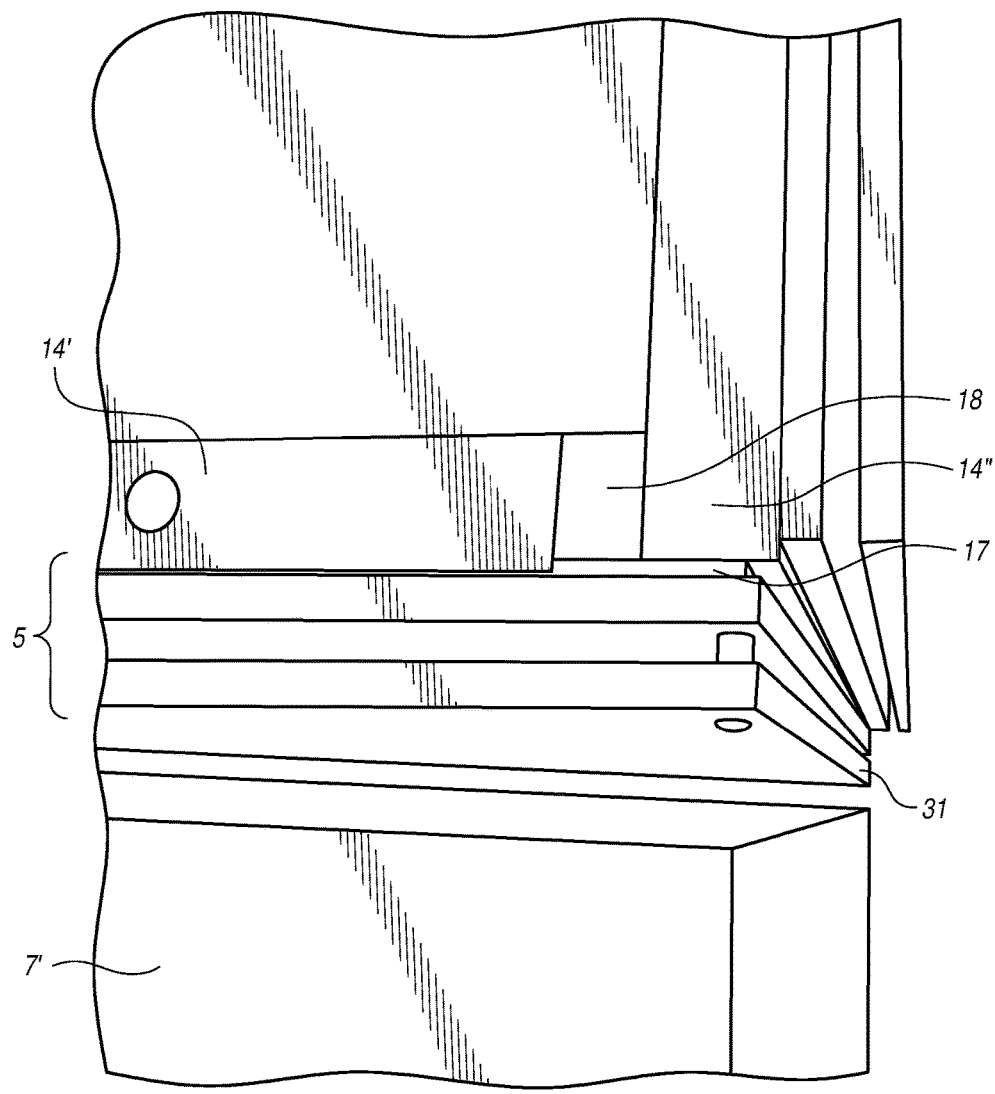
FIG. 6 shows a top view of a corner of an exemplary inner containment structure of a calorimetric measuring unit in relation to an exemplary embodiment of the invention.
Figure 7:
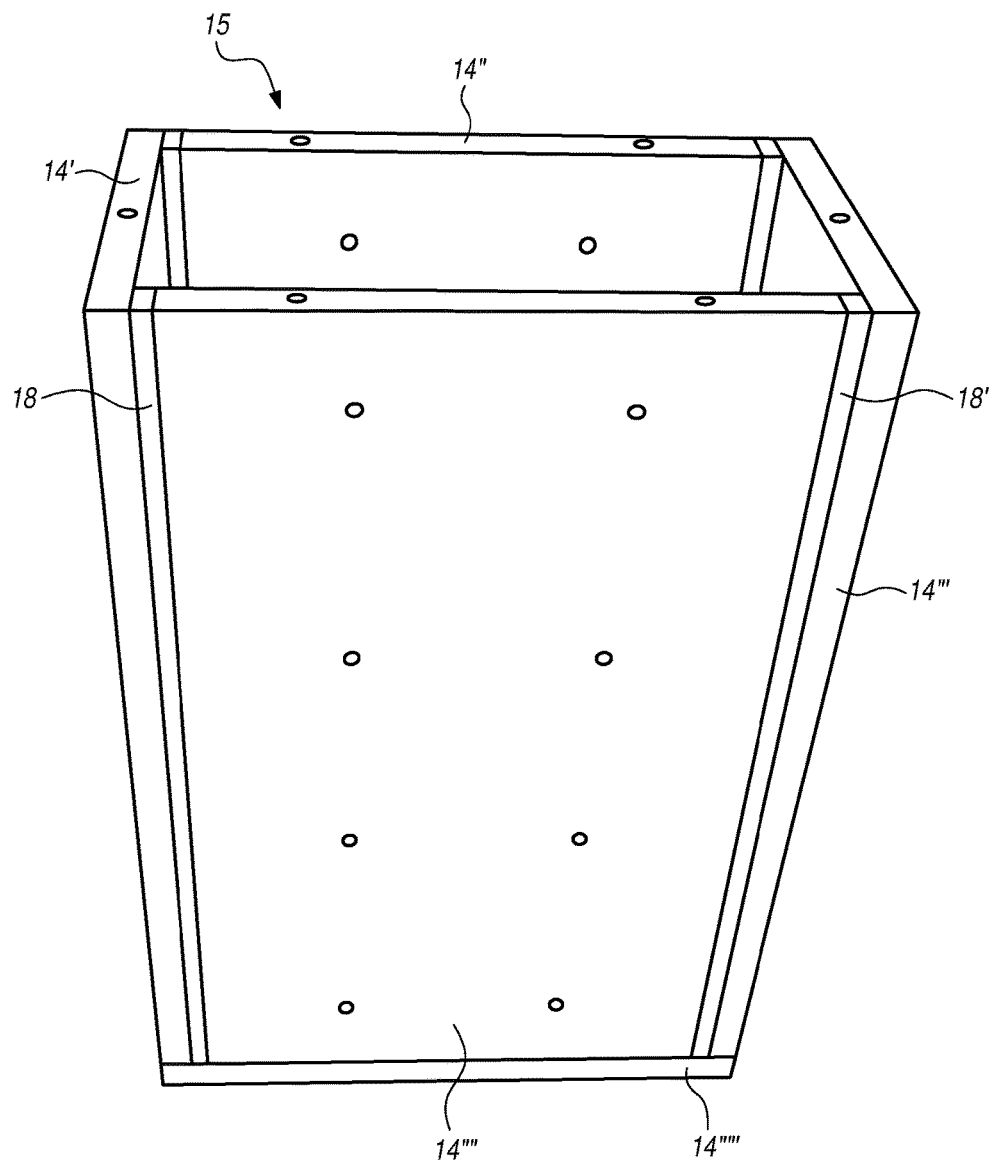
FIG. 7 shows an exemplary inner containment structure with thermal isolation barriers in relation to an exemplary embodiment of the invention.

FIGS. 5, 6, and 7 show thermal isolation barriers 17 used in relation to embodiments of the invention. Thermal isolation barriers are used in some embodiments to isolate thermal sensor assemblies from edge sections of adjacent sides of the inner containment structure 15. As shown in FIG. 6, a thermal isolation barrier 17 is disposed between one sensor assembly 5 and an adjacent inner containment structure section 14" (e.g., a side) that is parallel and adjacent to an inner containment structure section 14' that is parallel and in contact with the body of thermal sensor assembly 5. A different thermal isolation barrier 18 is disposed between inner containment structure section 14' and adjacent inner containment structure 14' that is, in this embodiment, an end side of the inner containment structure 15 forming two sides of the inner containment structure 15. Thermal isolation barriers, e.g., 17, inserted between edges of adjacent sections such as inner containment structure sections and thermal isolation barriers serves to ensure that heat data for each side of sample 3 can be measured independently from the other sides to avoid unmeasured thermal contributions to any thermal sensor assembly that are not oriented towards a face of inner containment structure 15. For example, when sample 3 is charged, heat data can be generated for each side of sample 3 facing a thermally isolated section or side of the inner containment structure independent of the other section or sides. If no thermal isolation barriers, e.g., 17, are used, then calorimetric measuring unit 1 would generate only one measurement for the total heat flow generated by sample 3. Embodiments can also include non-thermally conductive contact between outer surface (e.g., 21) of each sensor assembly, e.g., 5, and thermal isolation barriers, e.g., 17; such contact would not allow for individualized and independent heat data measurements for each thermally isolated section of inner containment structure 15.

In one exemplary embodiment, one or more thermal isolation barriers, e.g., 17, can comprise a gasket made of a small silicone sheet that is located between sensor assembly 5 and inner containment structure 15. In another exemplary embodiment, one or more thermal isolation barriers, e.g., 17, can comprise a thermal isolation strip made of clear polycarbonate located between sides of inner containment structure 15.

FIGS. 6 and 7 show another type of thermal isolation barrier 18 positioned with respect to different components as the previously discussed thermal isolation barriers, e.g., 17. As shown in FIGS. 6 and 7, thermal isolation barriers 18, 18' can be positioned between inner containment structure sections 14, 14' (e.g., sides). Likewise, additional thermal isolation barriers can be inserted between each inner containment structure section and each adjacent inner containment structure section to thermally isolate each inner containment structure section (e.g., side walls as well as floors and top section) from each other section. Thermal isolation barriers 18, 18', etc. operate in conjunction with thermal isolation barrier 17, 17', etc. to create an isothermal environment and to ensure that the heat data for each side of sample 3 can be measured independently from the other sections (e.g., sides) of the inner containment structure 15.

Figure 8:
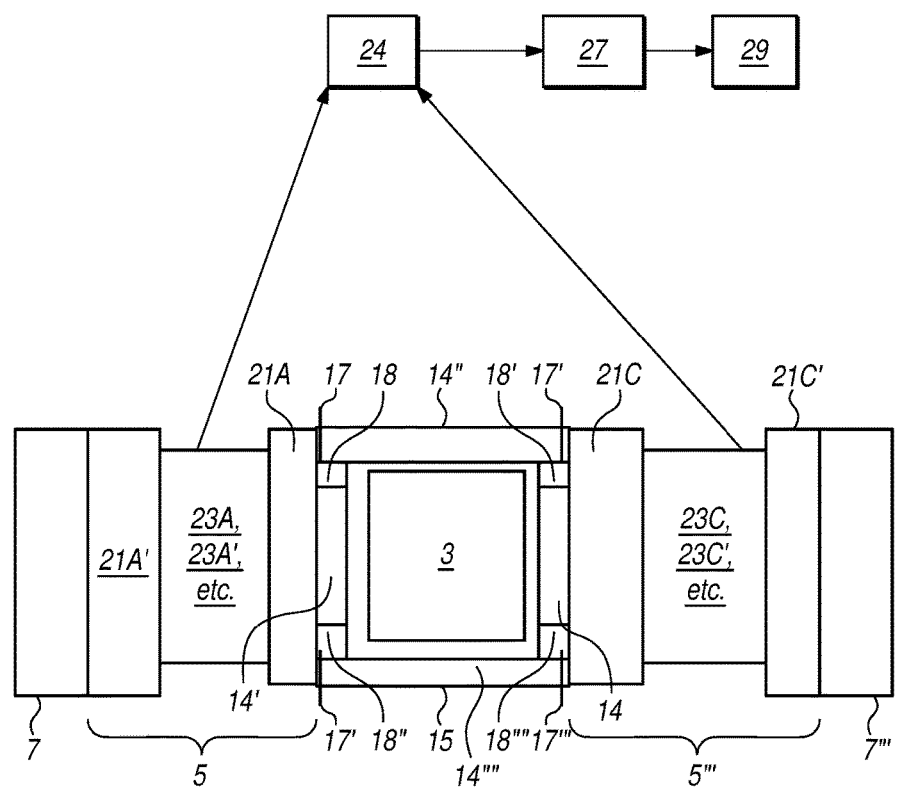
FIG. 8 shows a cross sectional diagram with top and bottom units removed in relation to an exemplary embodiment of the invention.

FIG. 8 shows a partial cross-sectional top view of exemplary calorimetric measuring unit 1 excluding top and bottom portions (each having thermal sensor assemblies and heat sinks along with thermal isolation barriers isolating them from side sections of the inner containment structure 15) as well as two of four side thermal sensor assemblies 5', 5" and heat sinks 7', 7". Exemplary inner containment structure 15 is shown with a sample 3 inside it. Thermal isolation barriers 17, 17', 17", and 17''' are disposed adjacent to outer edges of inner containment structure 15 sides. Another set of thermal isolation barriers 18, 18', 18", 18''' are disposed between sides of inner containment structure sections 14, 14', 14", 14'''. Edge sections of thermal sensor assemblies e.g., 5, 5''', are disposed adjacent to thermal isolation barriers 17, 17' and 17", 17''' respectively. Heat sinks 7 and 7''' are adjacent to sensor assemblies 5, 5''' respectively and outer containment structure 19 (not shown).

Figure 9:
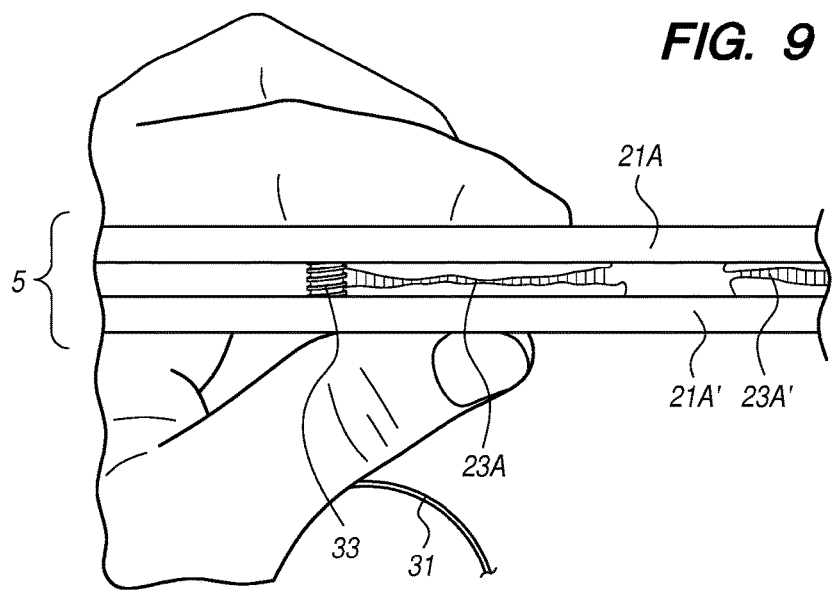
FIG. 9 shows an exemplary thermal sensor assembly used in an exemplary calorimetric measurement unit in accordance with an exemplary embodiment of the invention.

FIGS. 8 and 9 show components of sensor assembly 5. Assembly 5 comprises of two thermally conductive surfaces 21A and 21A' and a plurality of thermopiles 23A, 23A', etc. between them which conduct heat between the two surfaces 21A, 21A'. Thermopiles 23A, 23A' measure the heat flow as it passes through them and sends that measurement value to a data acquisition system 25 (shown in FIG. 8). A thermal sensor assembly, e.g., 5, is provided for each side, top, and bottom of the inner containment structure 15. This allows for individualized, independent measurements for each side of sample 3 facing a thermally isolated measuring section of the inner containment structure 15.

Figure 11:
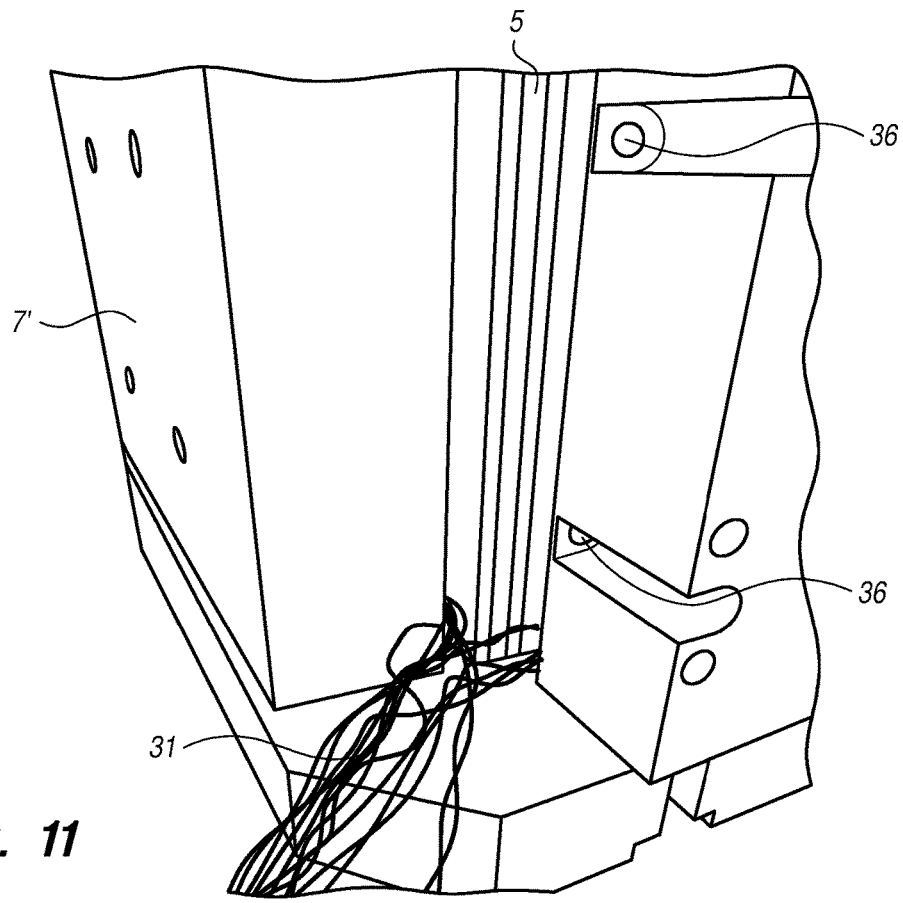
FIG. 11 shows an exemplary orientation of a wiring system for thermopiles with respect to an inner containment structure in accordance with an exemplary embodiment of the invention.
Figure 12:
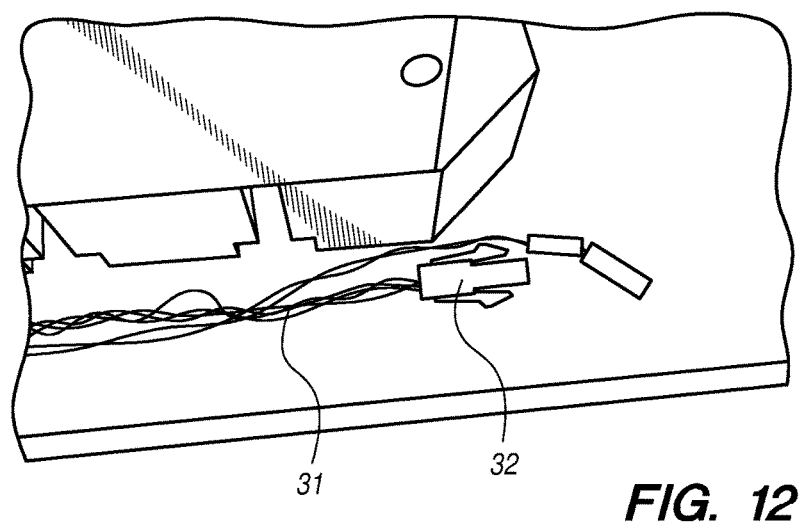
FIG. 12 shows exemplary data signal wires from an exemplary thermal sensor assembly terminating in a quick release electrical connector in accordance with an exemplary embodiment of the invention.

Referring back to FIG. 8, when sample 3 inside the inner containment structure 15 generates heat such as a during a charge cycle, the heat flow moves from sample 3 to the adjacent sensor assembly 5. Within sensor assembly 5, heat flows through thermally conductive surface 21, thermopiles 23A, 23A', etc., and a second thermally conductive surface 21A'. As heat moves from thermopiles 23A, 23A', etc. to a second thermally conductive surface 21, a measurement value is sent from thermopiles 23 to a connected data acquisition system 25. Data acquisition system 24 is connected to the plurality of thermopiles 23A, 23A', etc. through a set of separate wires 31 for each sensory assembly 5 as shown in FIGS. 11 and 12 which in turn is connected to a processing system 27 and an output system 29. In one embodiment, the thermopiles are arranged as such to be thermally in parallel but electrically in series. Such a mechanism for heat flow is present for each side inner containment structure 15 as heat would flow through the side's thermopiles generating a measurement value for data acquisition system 24. When sample 3 consumes thermal energy for a process the heat flow reverses direction in such that heat from the bath flows back through the system and into the system resulting in an opposing measurement.

From data acquisition system 24, a measurement value then is sent to a connected processing system 27. In an exemplary embodiment, processing system 27 contains a GPIB/Ethernet input/output section and has a processor and a storage medium box within the overall processing system box. From there, the measurement value is sent to an output device 29 which displays or outputs the information. In another exemplary embodiment, the output device can be a printer or a display. Measurements for each sensory assembly 5 can be done separately for each inner containment structure 15 facing different sides of sample 3.

In an exemplary embodiment shown in FIG. 9, sensor assembly 5 has two thermally conductive surfaces 21A, 21A' that are held together by a non-heat conductive bolt 33.

Figure 10:
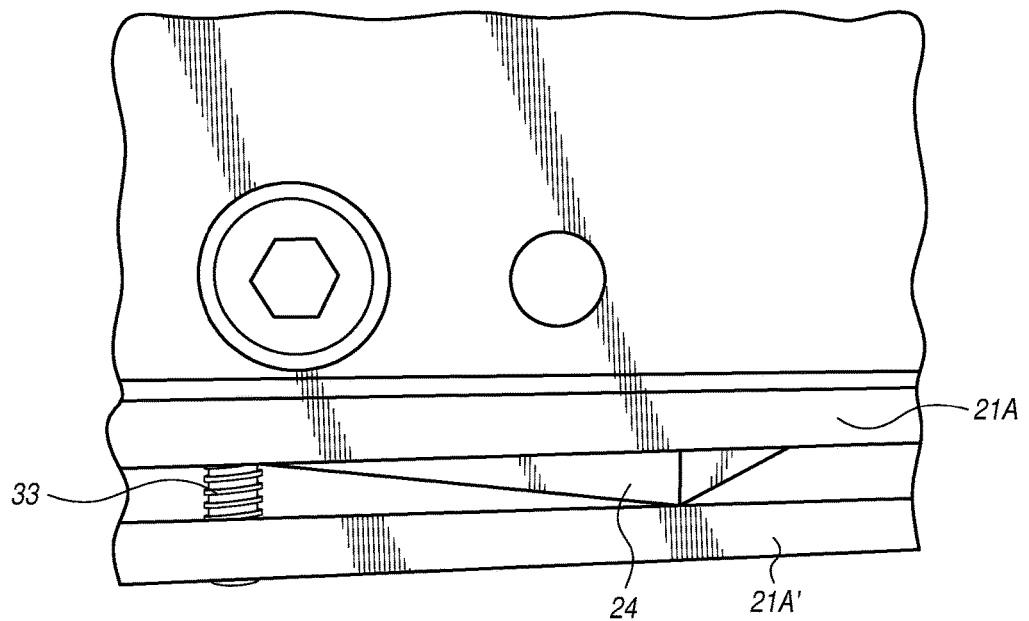
FIG. 10 shows an exemplary thermal sensor assembly attached to an inner containment structure of a calorimetric measuring unit in accordance with an exemplary embodiment of the invention.

FIG. 10 shows an exemplary thermal sensor assembly 5 attached to an inner containment structure 15. Sensor assembly 5 has thermally conductive surfaces 21A, 21A' that are held together by a non-heat conductive bolt 33. Spacer 24 is made from a non-conductive material and operates, in this embodiment, to prevent the thermopiles in thermal sensor assembly 5 from becoming damaged by a force applied to either of the thermally conductive surfaces 21A, 21A'.

As shown in FIG. 11, a non-heat conductive bolt(s) (not shown) goes through the thermally conductive surfaces at recessed areas 36 in heat sinks (e.g., 7, 7', etc.) and attaches to inner containment structure 15 through thermal sensor assembly 5. There is also spacer 24 in another exemplary embodiment. Spacer 24 is made from a non-conductive material and operates to prevent the thermopiles from becoming damaged by a force applied to either of the thermally conductive surfaces 21A, 21A'.

In an exemplary embodiment, the wires 31 terminate in common plugs 32 as shown in FIG. 12. Plugs 32 allow for greater ease of use with the data acquisition system 25 as the user can quickly disconnect the system by pulling plugs at the calorimetric measuring unit rather than splicing wires as in prior systems.

Figure 13:
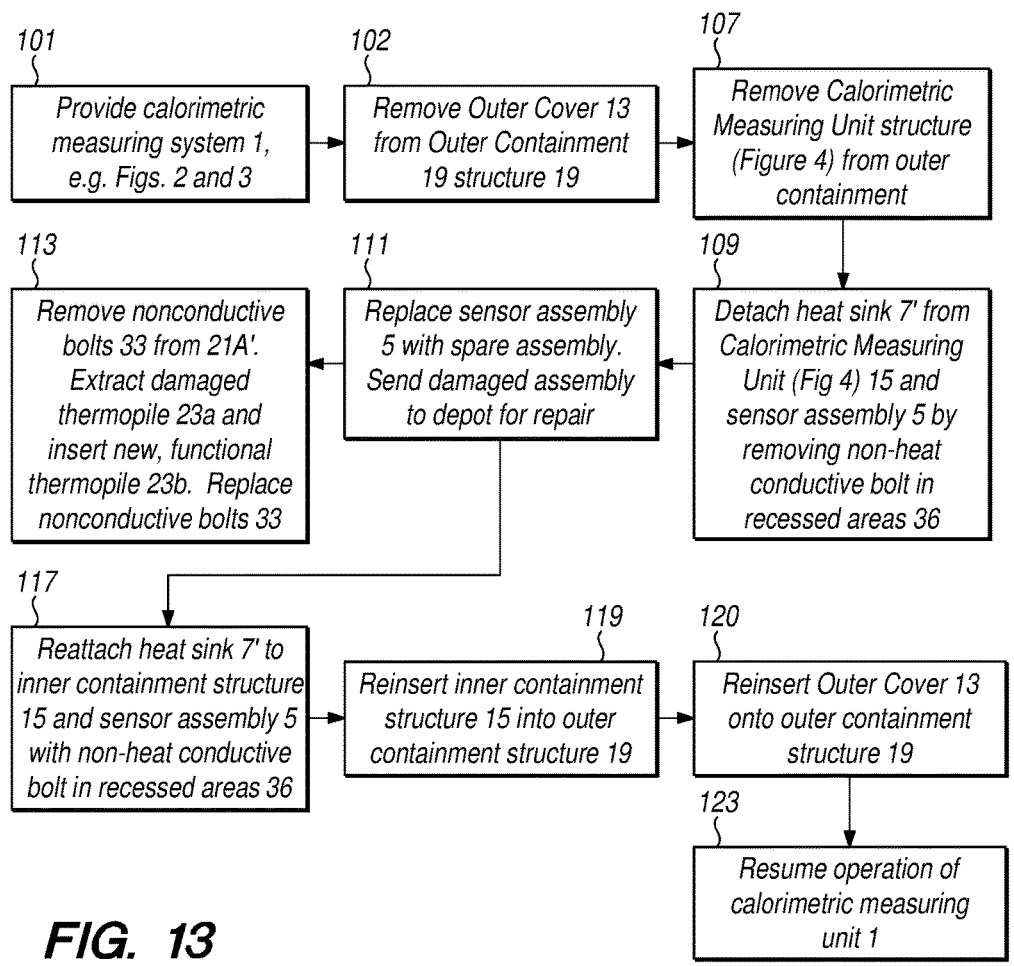
FIG. 13 shows a flow chart depicting an exemplary simplified method of repair for a calorimetric measuring unit in relation to an embodiment of the invention.

Referring to FIG. 13, a method of repair of a system in accordance with an embodiment of the invention is shown that can include providing an assembly comprising a calorimetric measuring system 1, e.g. FIGS. 2 and 3, such as described herein at step 101. At step 102, when it is determined by the user that thermopiles 23 need to be replaced, remove outer cover from outer containment structure 19. At step 107 remove inner containment structure 15 from outer containment structure 19. For example, step 107 can be accomplished by a use of lifting eye bolt 35 (e.g., shown in FIGS. 2, 3, 4). Next, according to step 109, heat sink 7' is detached from inner containment structure 15 and thermal sensor assembly 5 by the removal of non-heat conductive bolt(s) at recessed areas 36. Replace thermal sensor assembly 5 with a spare assembly as in step 111. Next, process continues by sending a faulty unit, e.g., thermal sensor assembly 5, back to the repair facility for step 113 and proceeding to step 117 for in field repairs. At step 113, outer heat sink wall section 21A' is detached from the thermal sensor assembly 5 with the removal of at least one non-heat conductive bolt 33. At step 113 a damaged thermopile(s) 23A can be extracted from inner heat sink wall section 21 and new functional thermopile 23B inserted into thermal sensor assembly 5. At step 117, heat sink 7 is reattached to thermal sensor assembly 5 and inner containment structure 15 and by the reinsertion of non-heat conductive bolts at recessed areas 36. At step 119, inner containment structure 15 is reinserted into outer containment structure 19. Proceeding to step 120, replace the outer cover over the outer containment structure 19. Operation of calorimetric measuring unit 1 can resume at step 123.

Figure 14:
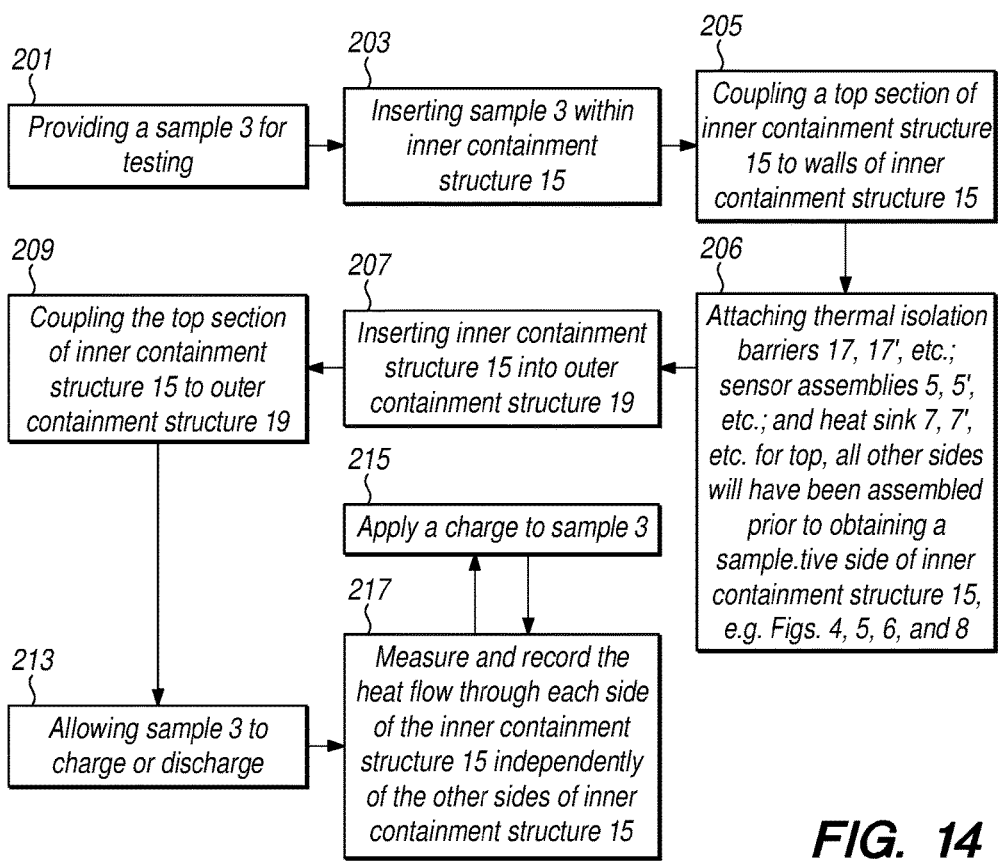
FIG. 14 shows a flow chart depicting an exemplary method of use for a calorimetric measuring unit in relation to an embodiment of the invention.

Referring to FIG. 14, a method of use of a system in accordance with an embodiment of the invention can include providing a sample 3 for testing at step 201. Sample 3 is then inserted within inner containment structure 15 at step 203. Then, at step 205, a top section of inner containment structure 15 is coupled to the walls of inner containment structure 15. At step 206, providing and coupling thermal isolation barriers 17, 17', etc.; thermal sensor assemblies 5, 5', etc.; and heat sink 7, 7', etc. for each respective side, top and bottom of inner containment structure 15 is accomplished (see, e.g. FIGS. 4, 5, and 8). Note that step 206 in this embodiment is performed prior to sample insertion; if no maintenance is required, this step does not need to be modified for each sample. Inner containment structure 15 is placed inside outer containment structure 19 according to step 207. Note with respect to step 207, in this embodiment structure 15 the heat sinks generally stay inside the outer containment structure 19 during changing of samples but are removable if necessary for a sample to be removed or inserted but such removal not required. At step 209, a top section of inner containment structure 15 is coupled to outer containment structure 19. At step 213, sample 3 is allowed to charge or discharge. At step 215, a charge is applied to sample 3, and at step 217, heat flow from sample 3 through each side of inner containment structure 15 is measured and recorded independently of the other sides of inner containment structure 15. Steps 213 to 215 can be omitted if sample 3 does not require a charge, such as with other sample types besides electrochemical energy storage devices. Charge and discharge profiles are sample dependent. The number of charges and discharges is variable from zero to any number as directed by the sample. The charge and discharge rates can also be variable or constant as required by the sample. Typically a charge and discharge program can be an established protocol that is normally completed without the addition of calorimetry, such as lot acceptance testing.

Figure 15:
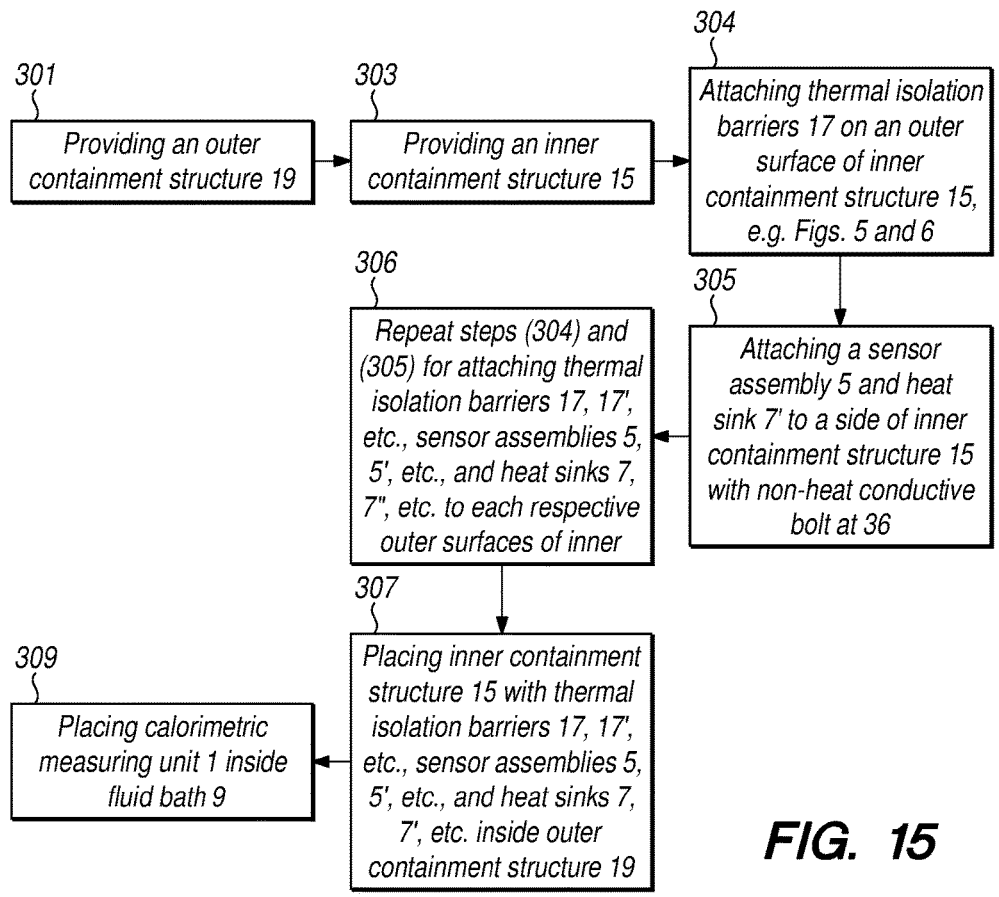
FIG. 15 shows a flow chart depicting an exemplary method of manufacture for a calorimetric measuring unit in relation to an embodiment of the invention.

Referring to FIG. 15, a method of manufacture of a system in accordance with an embodiment of the invention is shown that can include providing an outer containment structure 19 such as described herein at step 301. At step 303, an inner containment structure 15 is provided as well. At step 304, thermal isolation barriers 17, 17', etc. are attached on an outer surface of inner containment structure 15, e.g. FIGS. 5 and 6. At step 305, a thermal sensor assembly 5, 5', 5", etc. and a heat sink 7, 7', etc. are attached to each respective side of inner containment structure 15 with non-heat conductive bolt at recessed areas 36. At step 306, steps 304 and 305 are repeated such that thermal isolation barriers 17', 17", etc. and thermal sensor assemblies 5', 5" are attached to each respective outer surfaces of inner containment structure 15. At step 307, inner containment structure 15 with thermal isolation barriers 17, 17', etc.; thermal sensor assemblies 5, 5', etc.; and heat sinks 7, 7', etc. is placed inside outer containment structure 19 to form calorimetric measuring unit 1. Finally, at step 309, calorimetric measuring unit 1 is placed inside fluid bath 9. Note that step 309 can be moved to, e.g., initial setup, and thus leave the calorimetric measuring unit 1 inside the fluid bath for test operations and thus skip step 309 at this point of this exemplary process.

Figure 16:
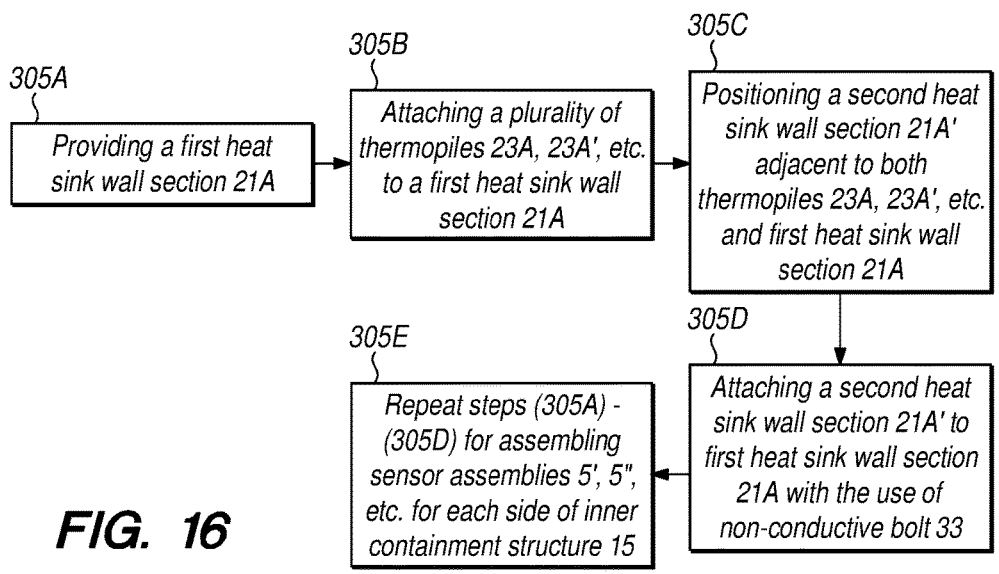
FIG. 16 shows a flow chart depicting an exemplary method of manufacture for a sensor assembly in relation to an embodiment of the invention.
Figure 17A:
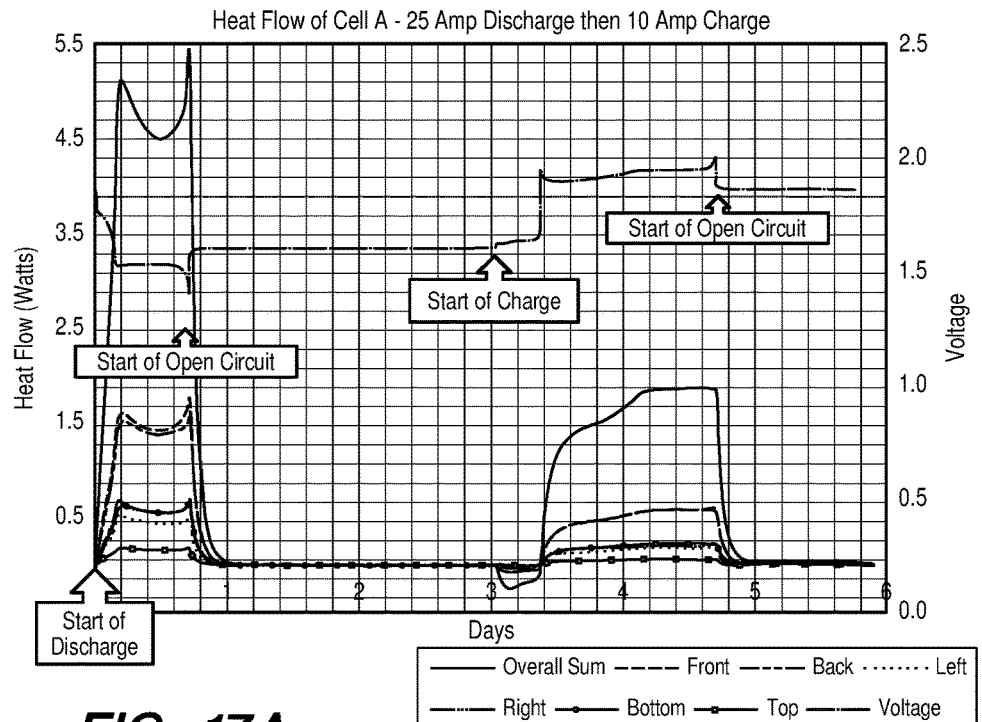
FIG. 17 shows exemplary heat flow curves showing individual signals for each surface of a sample cell from different sensor assemblies as well as the combined heat flow, which is the curve of largest value.
Figure 17B:
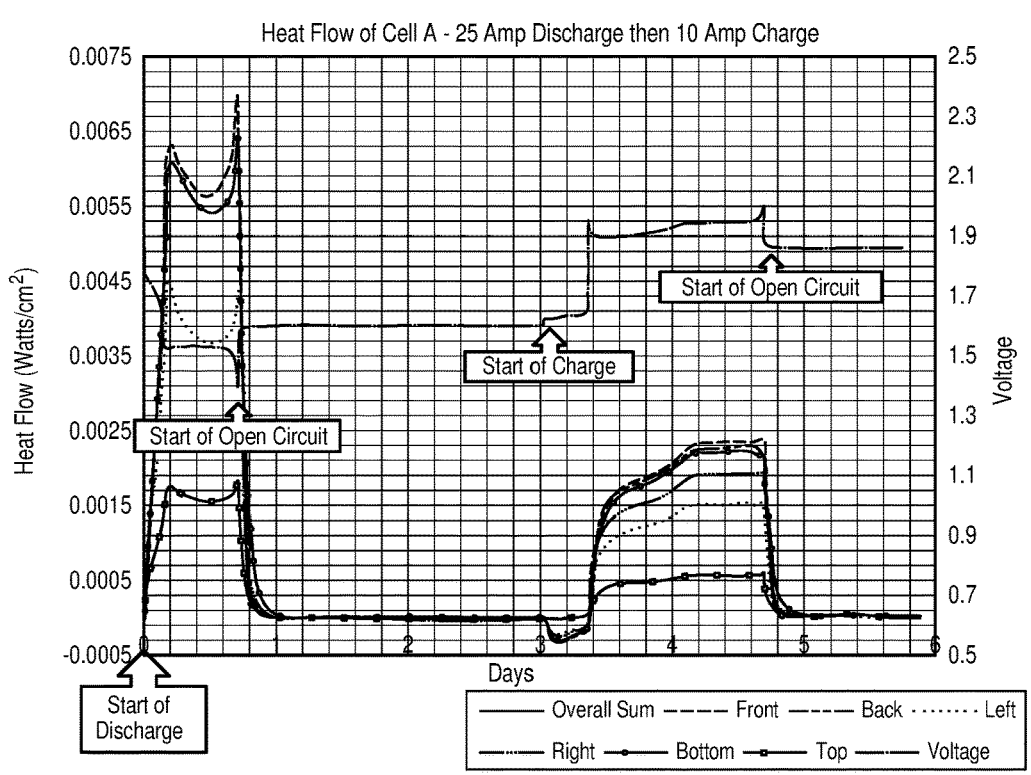
Figure 17C:
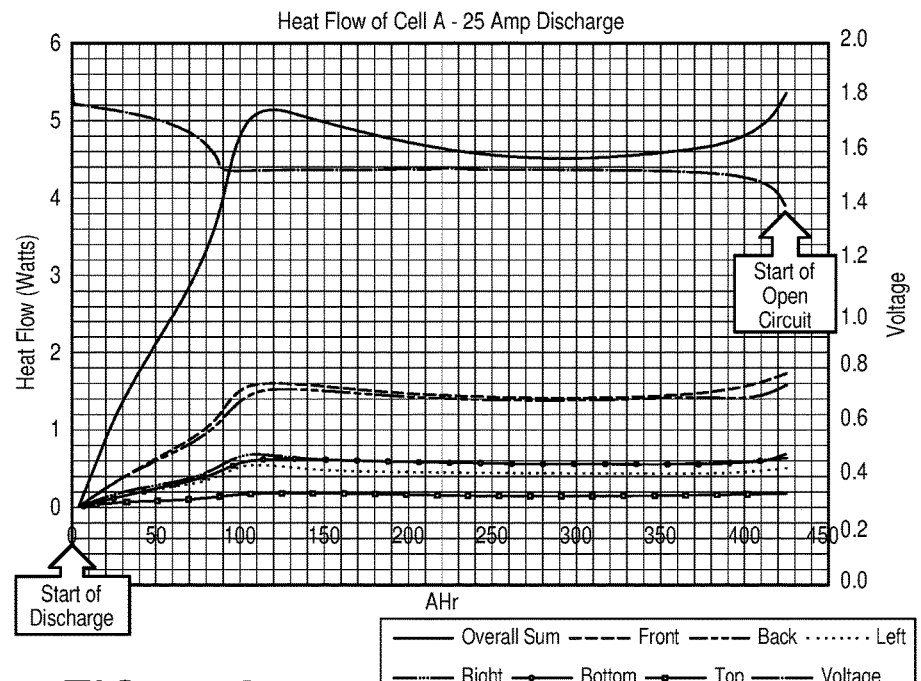
Figure 17D:
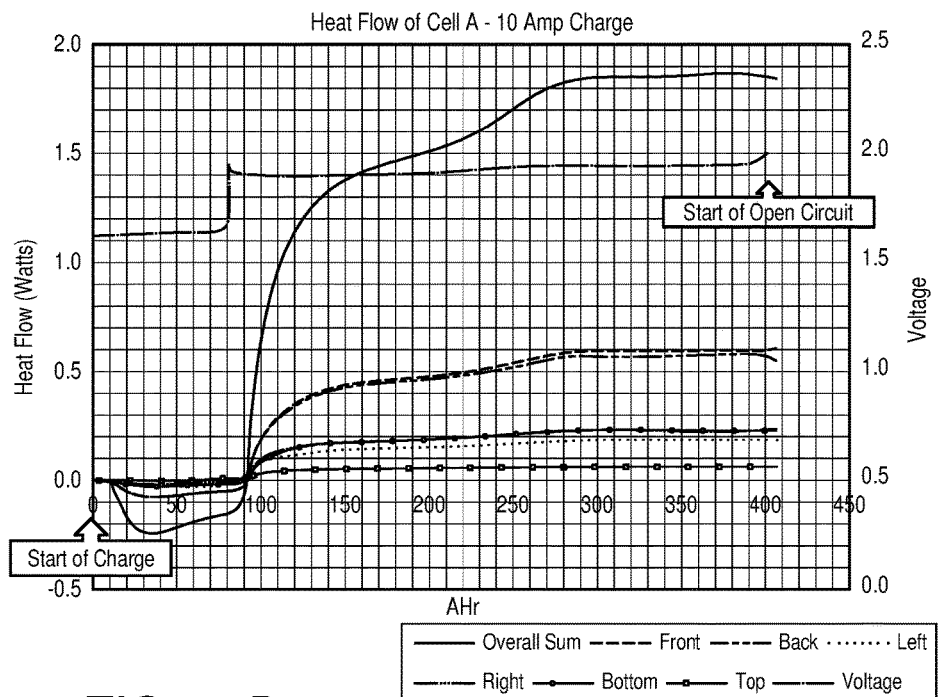

Referring to FIG. 16, an exemplary method of manufacture of a sensor assembly in accordance with an embodiment of the invention can include providing a first heat sink wall section 21A at step 305A. At step 305B, a plurality of thermopiles 23A, 23A', etc. are attached to first heat sink wall section 21A. In one embodiment, thermopiles 23A, 23A', etc. are adhered to first heat sink wall section 21A with a thermally conductive paste, improving thermal contact and providing a weak adhesive bond. At step 305C, positioning a second heat sink wall section 21A' adjacent to the thermopiles 23A, 23A', etc. and first heat sink wall section 21A. At step 305D, second heat sink wall section 21A' is attached to first heat sink wall section 21A with thermopiles 23A, 23A', etc. between the two surfaces. The heat sink wall sections 21 are secured to each other using non-heat conducting fasteners 33, such as PEEK bolts. At step 305E, steps 305A-305D are repeated for assembling thermal sensor assemblies 5', 5", etc. for each side of inner containment structure 15.

An exemplary calibration of the test system can be achieved through Joule heating. In one example, thermal conduction pathways also contain precision resistors or resistive heaters at fixed locations that are used to calibrate the thermopiles in that pathway by producing a known heat flow as calculated using Ohm's law. To ensure any "leakage" into unintended pathways is accounted for, each conduction pathway can be calibrated individually. Finally, one embodiment can include a point source placed in the approximate center of the test chamber and allowed to radiate thermal energy on to the collection surfaces of all of the pathways at the same time. The sum value is validated based on the calculated value of the point source. One exemplary calorimeter system constant was determined using silicon glass tubes filled with silicon glass beads as a known standard.

In one example, two silver-zinc cells were selected for calorimetry testing. A first can be designated Cell A with a weight of 4.32 kg when filled with electrolyte. A second cell can be designated Cell B with a filled weight of 4.11 kg. Heat capacity value for the exemplary samples was determined by changing the calorimeter bath temperature by 10° C. and then measuring the amount of energy absorbed into the test chamber in order to raise the cell to the new temperature and back into equilibrium with the calorimeter bath. This exemplary process was then repeated by lowering the calorimeter bath temperature to the original 25° C. Raising and lowering of the bath temperature was repeated again to provide a total of four separate heat flows to use in specific heat calculations.

In another example, once a heat capacity of the sample cell was determined, an exemplary cell was connected to the electrical test system and cycled according to the normal test plan for these cells. Both cells can be cycled at constant charge and discharge rates, including 10, 25, and 35 amps, inside the calorimeter. For each cycle, several plots, such as those shown in FIG. 18, can be generated including heat flow vs. time with an overlay of the voltage data, a normalized plot in which heat flow per surface area is compared for each surface of the sample cell (the top surface is inherently skewed low due to the measurement cell design), and heat flow vs. ampere hour plot for the discharge and charge steps.

Exemplary heat flow curves, e.g. FIG. 17, provide the individual signals for each surface of the sample cell as well as the combined heat flow, which is the curve of largest value. The start time for each time plot has been normalized to the start of the discharge step. The electrical cycling program was a discharge, rest, charge, and final rest. However, due to the transfer time required for the heat to move from the sample cell and across the measuring pathway the total thermal transfer time is longer than the time required for the individual electrical charge or discharge.

In an example, an average heat generated is calculated by integrating the area under a heat flow curve and then dividing by the time required for the electrical discharge, and not the longer time of total heat transfer.

In one example, charge or discharge number is the number in the calorimeter. Both sample cells in this example can be previously subject to normal lot acceptance testing prior to testing in the calorimeter. An interesting feature of an exemplary heat flow curve can be shown during a charging step. An endothermic portion can be observed at a start of each charging step.

Calorimetric data obtained during charge and discharge cycles was also used to determine the thermal efficiency of the sample cells. Total electrical energy for each charge or discharge was divided by the sum of the electrical energy and thermal energy.

Figure 18:
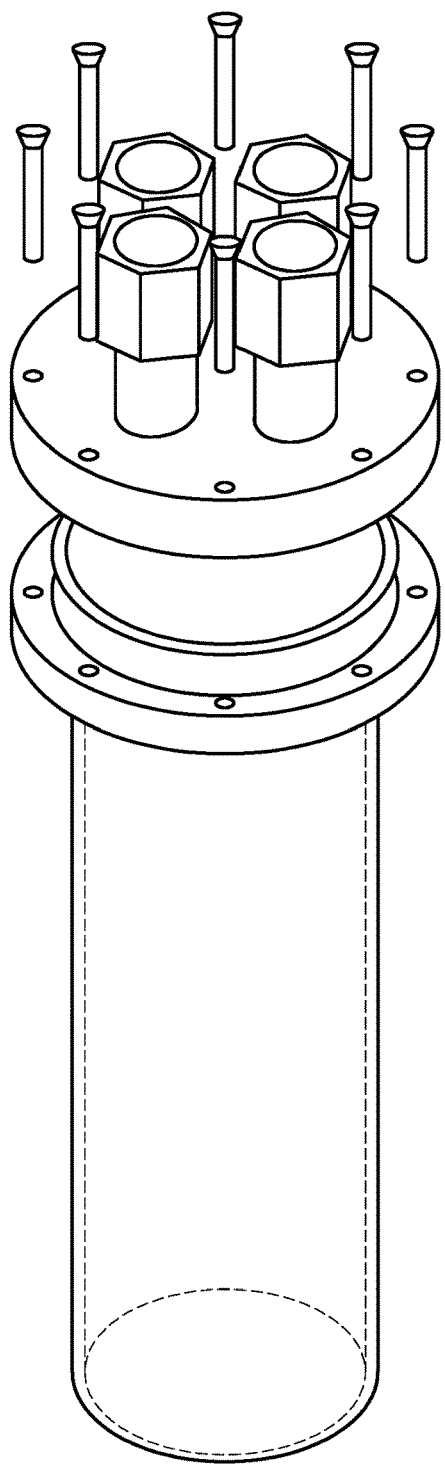
FIG. 18 shows an exemplary cell enclosure in accordance with one embodiment of the invention.

FIG. 18 shows an exemplary cell enclosure in accordance with one embodiment of the invention. Within the exemplary test cell enclosure 401, exemplary monitoring methods were used to capture test sample or battery cell characteristics through an overcharge test. A cylinder 403 is provided with an internal cavity 405 and a coupling section 407 that includes a flange 409 and bolt holes 411 as well as a seal well 413 adapted to receive a seal 415 which is used to provide a pressure seal with a lid section 417. Lid 417 includes multiple bolt holes 419 around a periphery which receive bolts 421 or fasteners that couple the lid section 417 to the flange 409. Sealing interface structures 423, 425, 427, and 429 are provided which screw into the lid section 417 which have apertures 431 which pass through the lid section 417 to permit instrumentation wiring or test structures to pass through the lid with an internal pressure seal structure which provides pressure containment for these sealed interface structures. Exemplary sealing interface structures 423, 425, 427, and 429 can include a variety of test related structures such as sections that permit different types of wires to pass into the test cell enclosure 401 which prevent gas or other elements from escaping the test cell enclosure 401 during destructive testing. Also, sealing interface structures can include an exhaust port, sensors such as pressure sensors, temperature sensors, etc.

Figure 19:
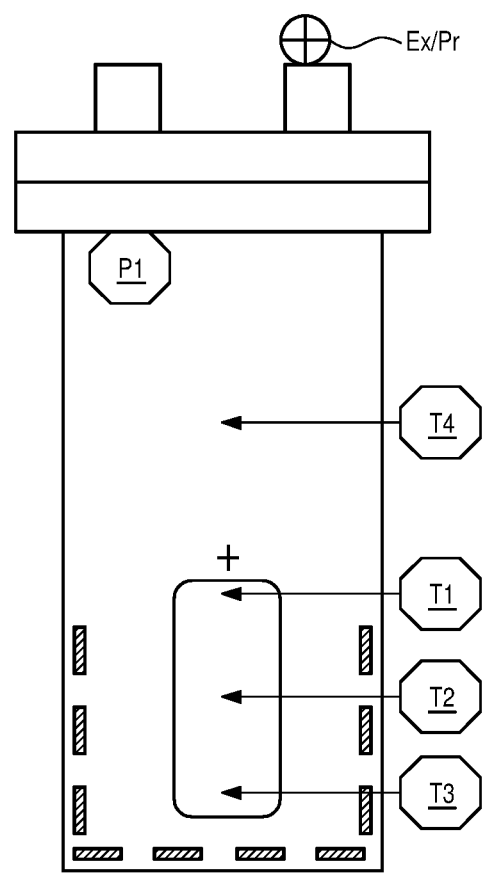
FIG. 19 shows a functional component diagram of an exemplary cell enclosure, such as for example, shown in FIG. 18.

FIG. 19 shows a functional component diagram of an exemplary test cell enclosure, such as for example, shown in FIG. 18, 401. In particular, FIG. 19 provides an overview of an exemplary test cell enclosure 401 layout. In this example, an exhaust valve/port (Ex/Pr) is provided as an interface structure 423 that couples with a threaded port formed into the lid section 417. Also, three K-type thermocouples can be placed on each test article within the exemplary test cell enclosure with wires that pass through the sealing interface structures, e.g., 427, 429; one located near a positive terminal (T1), one at a test article center (T2), and one near a negative terminal (T3). An additional thermocouple (T4) can be placed above the test article (e.g., Lithium battery) near the cell enclosure 401 cylinder opening defined by the flange 409 to monitor the test cell enclosure's 401 ambient temperature. A pressure transducer P1 can be placed above the cell at the enclosure lid or cover 417 to collect data on forces generated from a destructive test event, e.g., a Lithium battery overcharge event. Data can be collected utilizing a high speed data acquisition device (not shown) can be connected to wires and test instrumentation displayed in FIG. 19.

Figure 20:
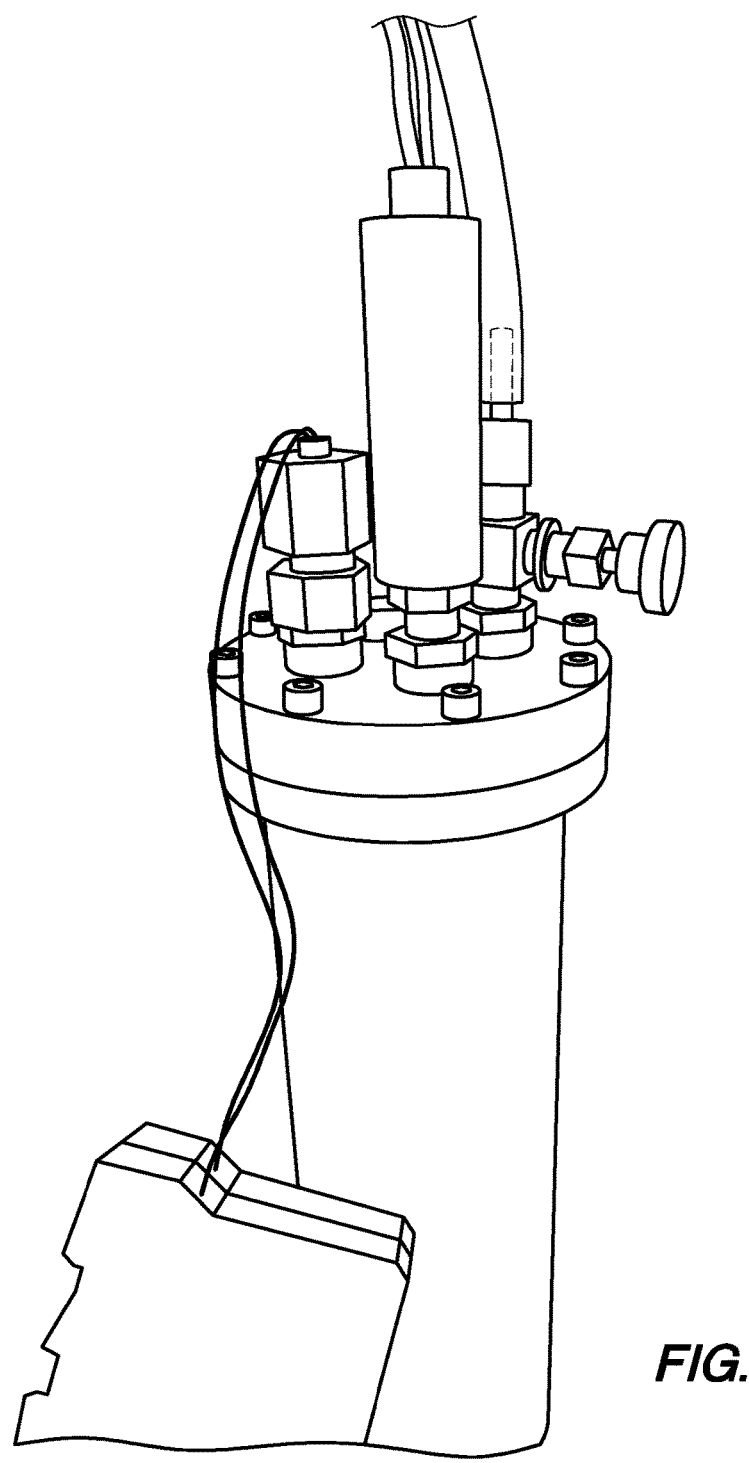
FIG. 20 shows an exemplary cell enclosure in accordance with one embodiment of the invention.

FIG. 20 shows another view of the FIGS. 18 and 19 exemplary cell enclosure in accordance with one embodiment of the invention.

Figure 21:
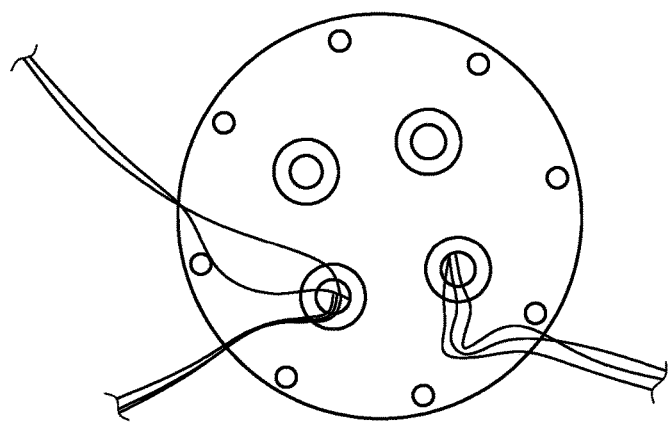
FIG. 21 shows an bottom view of a removable top section of the exemplary cell enclosure of FIG. 20.

FIG. 21 shows a bottom view of a removable top section of the exemplary cell enclosure of FIG. 20 with test instrumentation wires coming out of ports or apertures in the lid 417.

Figure 22:
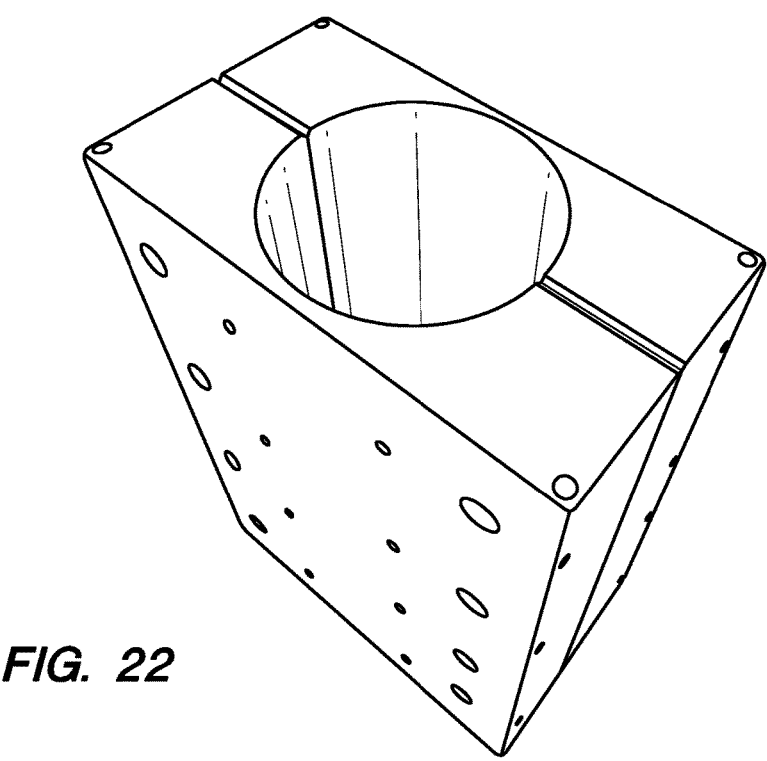
FIG. 22 shows a perspective view of one exemplary embodiment of the invention that can use an aluminum block or adapter that can be used as a substitute or alternative embodiment to an exemplary inner containment structure (e.g., see FIG. 7, 15) that an exemplary cell enclosure (e.g., FIGS. 18-20) inserts into and is further adapted to have thermal sensor assemblies attached to different sides for use with a calorimetric measuring unit.

FIG. 22 shows a perspective view of one exemplary embodiment of the invention that can use an aluminum block or adapter 431 that can be used as a substitute or alternative embodiment to an exemplary inner containment structure (e.g., see FIG. 7, 15) that an exemplary cell enclosure (e.g., FIGS. 18-20) inserts into and is further adapted to have thermal sensor assemblies attached to different sides for use with an exemplary calorimetric measuring unit. In particular, exemplary cell enclosure 401 can be placed within a solid aluminum block with an aperture formed to receive the exemplary cell enclosure, e.g., enclosure 401 of FIG. 18-21, to facilitate good thermal contact with a calorimeter measuring sensors 5 attached to different sides of the block 431 (top, bottom, and sides) for testing. An exemplary calorimeter measurement assembly with the block or adapter 431 can include six isolated thermal pathways, one for each planar surface of the cuboid block, that are coupled to each side with a heat sink attached on an opposing side of the sensors 5 (e.g., see FIGS. 4-11). In some embodiments, due to a solid nature of the block or adapter 431 substitute for inner containment structure 15 and round shape of the test cell enclosure 401 and fixturing requirements the five measuring surfaces available in the above disclosed embodiment with inner containment structure 15 were no longer isolated (which requires thermal isolation barriers) and thus generated a sum heat flow value. Each of the five surfaces had at least six and up to eight thermopiles for a total of approximately forty. An alternative embodiment can include cutting the exemplary test cell enclosure 401 into segments and separating them with thermal isolation barriers which then are surrounded by the block or adapter (e.g., alternative inner containment structure 15') which is similarly segmented with thermal isolation barriers (not shown) which then have separate thermal sensor units and heat sink assemblies or sets respectively attached to the segmented sections to permit directional or vector analysis of where heat flows are originating in the sample or test article. Data can be recorded on an Agilent® 34972a LXI data acquisition device.

Due to the size and anticipated thermal loading of the intended sample, this exemplary calorimeter was not designed to compare heat flow from a matched reference chamber. Inclusion of a reference chamber would serve to decrease measurement noise for more precise measurements.

Figure 23:
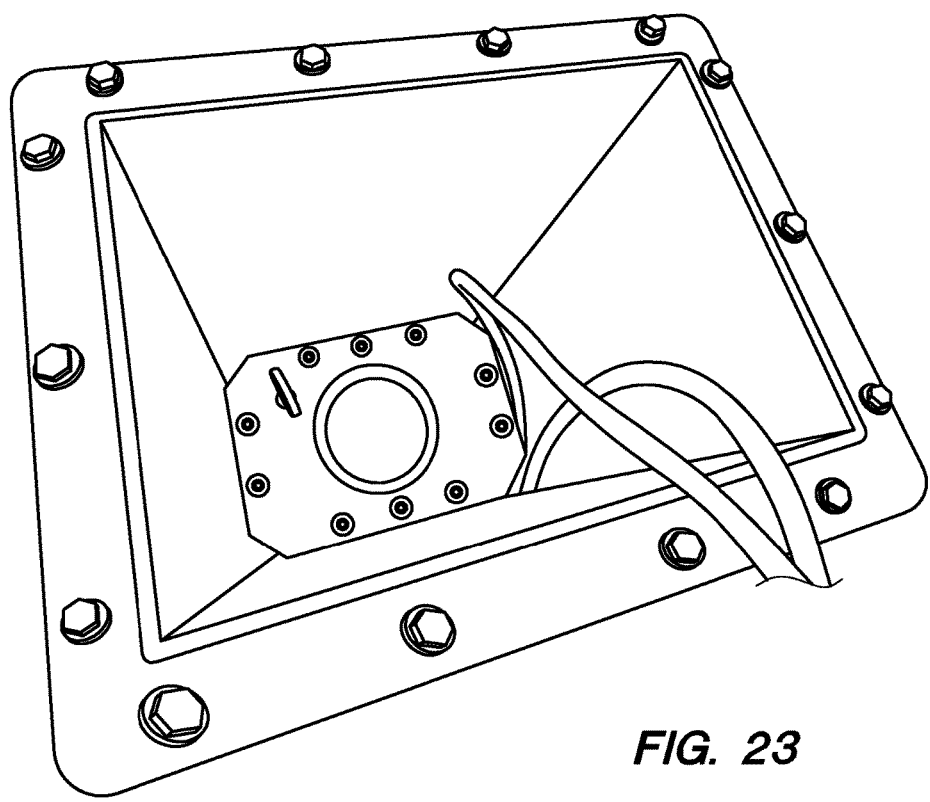
FIG. 23 shows an exemplary FIG. 22 alternative inner containment structure (15'), sensors (5), and heat sinks (7, et. al.) assembly installed within an exemplary outer containment structure which in turn inserts into a fluid bath (e.g., see FIG. 1, 9) that is in turn contained within calorimetric measuring unit 1 (e.g., see FIG. 1, 2)

FIG. 23 shows an exemplary FIG. 22 alternative inner containment structure 15', aluminum block or adapter formed to receive exemplary test cell enclosure such as shown in FIGS. 18-21, sensors 5, and heat sinks 7, et. al. assembly installed within an exemplary outer containment structure which in turn inserts into a fluid bath (e.g., see FIG. 1, 9) that is in turn contained within calorimetric measuring unit 1 (e.g., see FIG. 1, 2).

Figure 24:
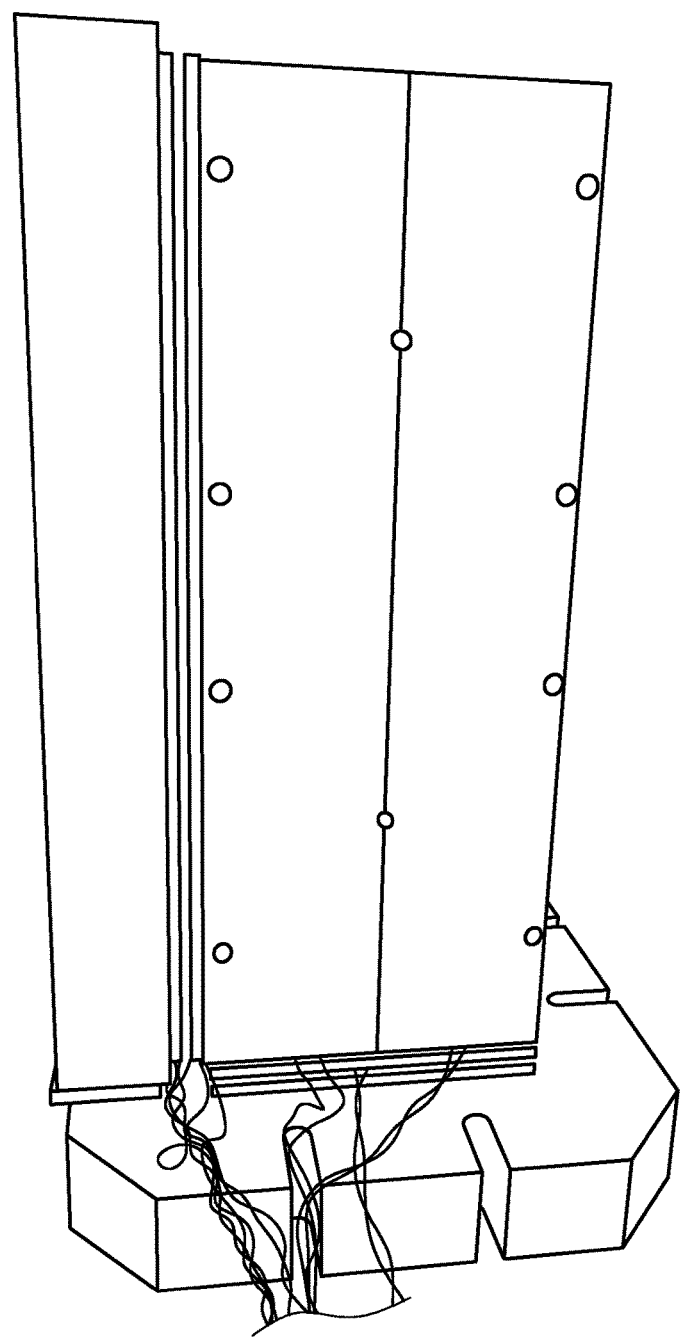
FIG. 24 shows an exemplary embodiment of the FIG. 22 aluminum block or adapter with an exemplary FIG. 22 alternative inner containment structure (15'), sensors (5), and heat sinks (7, et al) assembly.

FIG. 24 shows an exemplary embodiment of the FIG. 22 destructive event inner containment structure 15'(aluminum block or adapter) that replaces previously described inner containment structure (e.g., 15), thermal sensors (e.g., 5), and heat sinks (e.g., 7, et al) assembly. Six sets of thermal sensors and heat sink assemblies are mechanically and thermally coupled to each side of the inner containment structure 15' block or on all sides and top and bottom.

Figure 25:
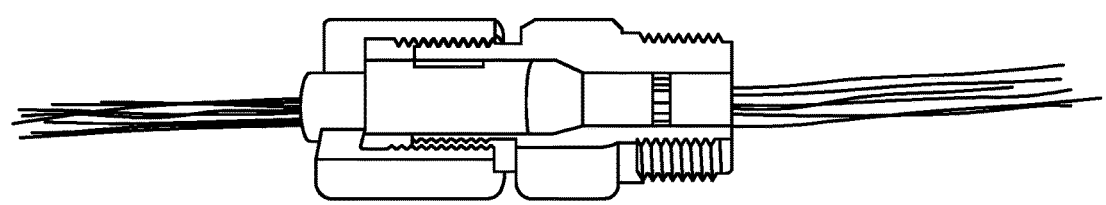
FIG. 25 shows an exemplary sealing interface structure that screws or couples with the exemplary test cell enclosure that is used to pass or interface test instrumentation wires or conduits through a section, e.g., a lid, of the exemplary test cell enclosure (e.g., see FIGS. 18-20).

FIG. 25 shows an exemplary sealing structure used to interface test instrumentation wires or conduits through exemplary test cell enclosure (e.g., see FIGS. 18-20). In this example, a Conax Technologies® power lead seal structure is shown with a two part cap and body which threadedly engage each other. A wire passes through a center section of the cap and body which are sealed with a Teflon sleeve, follower, sealant, insulator, and another Teflon sleeve which are placed within the cap and body surrounding the wire(s) that pass through the cap/body. Sealant structure can include a liquid or soft sealant that provides a sealing structure (e.g., when screwed together the sealant is deformed into the cap/body to provide a seal). This exemplary sealing interface structure body has threads which are screwed into the cap section 417. These sealing interface structures are adapted to seal against gases or liquids and resists element movement through the sealing interface structure under pressure.

Although the invention has been described in detail with reference to certain preferred embodiments, variations and modifications exist within the spirit and scope of the invention as described and defined in the following claims.

The invention claimed is:

1. A testing system comprising:
    a temperature calibration bath structure having an interior section adapted to contain and thermally control a thermally conductive fluid, wherein said calibration bath is adapted to accept or donate thermal energy;
    an outer containment structure formed to fit within said interior section and be disposed within said fluid, said outer containment structure is further formed having a plurality of outer containment structure sections comprising first side sections, a first top section and a first bottom section, wherein at least one outer containment structure section is selectively removable or operable to permit access to an interior section of said outer containment structure, wherein said outer containment structure is formed so as to prevent said fluid from passing into said interior section, said outer containment structure is formed from heat conductive material;
    a plurality of heat sinks having a first side and an opposing second side, wherein said first side is facing said outer containment structure, wherein each said heat sink is thermally coupled along thermal conductive paths along a plurality of lateral axis where one of each said plurality of lateral axis passes respectively through each of said heat sinks extending orthogonally away from a vertical axis through a center of said outer containment structure that is parallel to at least one side of said outer containment structure, said thermally conductive paths including thermally conductive bolts and finally through the outer containment structure, wherein each of said plurality of heat sinks are thermally isolated from adjacent said heat sinks that are not along said respective plurality of lateral axis;
    a plurality of thermal sensor assemblies having a first and second side, each of said plurality of thermal sensor assemblies are respectively thermally and removably coupled on said first side to the second side of said heat sinks, wherein each of said thermal sensor assemblies is physically separated from each other, wherein each of said thermal sensor assemblies comprises a first and second heat sink wall section and a plurality of thermopiles, wherein said first and second heat sink wall sections are thermally separated by said thermopiles to form a thermoconductive path through each said thermopile;
    an inner containment structure operable to removably receive a test cell enclosure operable to receive a sample for thermal testing, wherein said plurality of thermal sensor assemblies are respectively thermally and removably coupled to said second sides of said inner containment structure, wherein said inner containment structure comprises a plurality of wall sections, including second side sections, a second top section and second bottom section, as well as a plurality of thermal isolation barriers, one of said plurality of thermal isolation barriers are each disposed between areas of said wall sections that couple with each other so as to thermally isolate each said wall section from another adjacent wall section, wherein each of said wall sections are selectively and removably coupled together with thermally non-conductive fasteners such as non-conductive screws formed to screw through a face of a wall section, through said respective thermal isolation barrier, and into an edge of an adjacent wall section in contact with the adjacent wall section, wherein said plurality of thermal sensor assemblies are formed so as their heat sink wall sections are substantially of the same length and width of respective surfaces of said inner containment structure wall sections they are facing;

wherein said test cell enclosure is formed to fit within said inner containment structure and facilitate heat transfer, said test cell enclosure further comprises a lid and a test cell enclosure body said lid couples with to prevent pressure of a force up to a first force from escaping, wherein said lid is further formed with a plurality of lid apertures that pass through the lid, said test cell enclosure further comprises a plurality of interface structures that coupled with the lid apertures, said interface structures comprise a pressure sensor and a plurality of pressure sealing wiring interface structures that permit test cell enclosure instrumentation wires to pass through the lid into the test cell enclosure, said test cell enclosure further comprises a plurality of test cell enclosure thermocouples which are disposed within the test cell enclosure structure, some of said test cell enclosure structures are physically coupled to a sample in a plurality of locations, wherein at least one test cell enclosure thermocouples are disposed spaced-apart from said sample but not touching said sample, wherein said interface structures further comprise an exhaust port configured to selectively release pressure contained within said test cell enclosure body accumulated after a destructive test event of said sample, one of said instrumentation wires comprise an electrical source wire configured to pass electrical current to said sample for destructive testing.

2. The testing system of claim 1 wherein said temperature calibration bath further comprises a stirrer or pump operable to circulate said fluid to facilitate a desired temperature of said fluid.

3. The testing system of claim 1 wherein said temperature calibration bath further comprises a temperature control mechanism comprising an integrated heater in a bottom plate of said temperature calibration bath and a cooling element at the top of said temperature calibration bath.

4. The testing system of claim 1 wherein each of said thermal sensor assemblies output separate measurement data to measure heat flow from respective faces of said sample oriented towards a respective wall section facing said sample, wherein said thermal sensor assemblies comprise thermopiles arranged as parallel thermal pathways but electrically connected in series to sum and amplify a generated signal from said thermopiles.

5. The testing system of claim 1 wherein said thermal sensor assemblies are configured to output separate measurements to independently measure heat flow from each side of said inner containment structure, wherein said thermal sensor assemblies comprise thermopiles arranged as parallel thermal pathways but electrically connected in series to sum and amplify a generated signal from said thermopiles.

6. The testing system of claim 1 wherein at least one thermal sensor assembly further comprises one or more non-heat conductive bolts or couplers that goes through said first and second heat sink wall sections and attaching to said inner containment structure so as to thermally couple said at least one thermal sensor assembly to said inner containment structure.

7. The testing system of claim 1 wherein at least one thermal sensor assembly further comprises a spacer adapted to prevent contact between said first and second heat sink wall section and thereby permit thermal energy to only pass between said heat sink wall sections through one or more said thermopiles disposed there between.

8. The testing system of claim 7 wherein said spacer is made from a non-thermally conductive material.

9. A method of repair of a testing system providing an assembly comprising:
providing a testing system comprising:
a temperature bath housing structure adapted to contain and maintain a fluid bath at a predetermined temperature;
an outer containment structure adapted to insert into the temperature bath housing structure in immersive contact with said fluid bath through an aperture;
an outer cover over said aperture in said outer containment structure;
an internal containment structure formed as a thermal sensor assembly enclosure formed to fit into said outer container structure and receive said internal containment structure, said thermal sensor assembly enclosure each comprises a plurality of walls including a first wall assembly, each of said plurality of walls comprise a layered structure having a thermal sensor assembly that has a first and second thermally conductive sheet or section on opposing sides of one or more thermal sensors forming thermally isolated conductive path or paths between said first and second thermally conductive sheets or sections, an outer heat sink in thermal contact with said first thermally conductive sheet or section, an inner heat sink in thermal contact with said second thermally conductive sheet or section, and a plurality of removable non-thermally conductive coupling structures coupling said outer heat sink, said walls and said inner heat sink together, said coupling structures do not extend from opposing sides of said walls, wherein each of said walls are thermally isolated from each other by thermal insulation or barrier structures so as to enable each of said thermal sensor assemblies measure heat flow into or out of the inner containment structure's different sections or sides; and
a test cell enclosure sized to fit into said internal containment structure that is adapted to contain forces and output from destructive testing of samples;
detecting or determining at least one of said thermal sensors in said first wall requires replacement;
commencing a repair operation comprising:
removing said cover from the outer containment unit;
removing said inner containment structure from said outer containment structure through said aperture;
removing one or more said non-thermally conductive coupling structures from said first wall and detaching one of said outer heat sinks coupled to said selected one of said walls;
replacing one of said thermal sensor assemblies within said first wall with a replacement thermal sensor assembly including at least one new said thermal sensors;
placing said first wall with said replacement thermal sensor assembly in contact with one of said inner heat sinks formerly in contact with said first wall;

placing one of said outer heat sinks formerly in contact with said first wall in contact with said replacement thermal sensor assembly;

reinserting said one or more said coupling structures into said first wall with said replacement thermal assembly;

reinserting said inner containment structure into said outer containment structure; and replacing the outer cover over the outer containment unit.

10. A method as in claim 9, further comprising the commencing of testing after said repair operation is completed.

11. A method as in claim 9, wherein said inner containment structure further comprises a top wall with an eye bolt, said method further comprising lifting said inner containment structure from said outer containment stricture using a lifting structure coupled to said eye bolt.

12. A method as in claim 9, wherein at least some of said thermal sensors are a thermopile.

13. A method as in claim 9, wherein said testing comprises separately detecting and recording heat flow through one, some or each said side from separate signal busses from each side.

14. A testing system comprising:
a temperature bath housing structure adapted to contain and maintain a fluid bath at a predetermined temperature;
an outer containment structure adapted to insert into the temperature bath housing structure in immersive contact with said fluid bath through an aperture;
an outer cover over the aperture in said outer containment structure;
an internal containment structure formed as a thermal sensor assembly enclosure formed to fit into said outer container structure and receive said internal containment structure, said thermal sensor assembly enclosure each comprises a plurality of walls including a first wall assembly, each of said plurality of walls comprise a layered structure having a thermal sensor assembly that has a first and second thermally conductive sheet or section on opposing sides of one or more thermal sensors forming thermally isolated conductive path or paths between said first and second thermally conductive sheets or sections, an outer heat sink in thermal contact with said first thermally conductive sheet or section, an inner heat sink in thermal contact with said second thermally conductive sheet or section, and a plurality of removable non-thermally conductive coupling structures coupling said outer heat sink, said walls and said inner heat sink together, said coupling structures do not extend from opposing sides of said walls, wherein each of said walls are thermally isolated from each other by thermal insulation or barrier structures so as to enable each of said thermal sensor assemblies measure heat flow into or out of the inner containment structure's different sections or sides;

a measuring system that measures outputs from each of said thermal sensors and determines a thermal data value associated with thermal energy passing through each thermally isolated said wall; and a test cell enclosure sized to fit into said internal containment structure that is adapted to contain forces and output from destructive testing of samples.

15. A system as in claim 14, wherein said inner containment structure further comprises a top wall with an eye bolt configured to enable lifting of said inner containment structure from said outer containment stricture using a lifting structure coupled to said eye bolt.

16. A system as in claim 14, wherein at least some of said thermal sensors are a thermopile.

17. A system as in claim 14, further comprising a plurality of separate signal busses that separately connect with said thermal sensors in each of said walls that separately transmits signals from said thermal sensors to a measurement device that detects and records heat flow through one, some or each said side that is thermally isolated from each adjacent said side.

* * * * *